(12) United States Patent
Panotopoulos et al.

(10) Patent No.: US 12,042,597 B2
(45) Date of Patent: Jul. 23, 2024

(54) FLUID EXCHANGE SYSTEM AND RELATED METHODS

(71) Applicant: IRRAS USA, Inc., San Diego, CA (US)

(72) Inventors: Christos Panotopoulos, Athens (GR); Lance Boling, San Jose, CA (US); Tim Kovac, Anderslov (SE); Kleanthis Xanthopoulos, La Jolla, CA (US)

(73) Assignee: IRRAS USA, Inc., San Diego, CA (US)

( * ) Notice: Subject to any disclaimer, the term of this patent is extended or adjusted under 35 U.S.C. 154(b) by 1179 days.

(21) Appl. No.: 16/489,774

(22) PCT Filed: Mar. 19, 2018

(86) PCT No.: PCT/IB2018/051838
§ 371 (c)(1),
(2) Date: Aug. 29, 2019

(87) PCT Pub. No.: WO2018/167740
PCT Pub. Date: Sep. 20, 2018

(65) Prior Publication Data
US 2020/0237977 A1 Jul. 30, 2020

Related U.S. Application Data

(60) Provisional application No. 62/473,303, filed on Mar. 17, 2017.

(51) Int. Cl.
*A61M 1/00* (2006.01)
*A61B 5/03* (2006.01)
*A61B 17/22* (2006.01)

(52) U.S. Cl.
CPC ............... *A61M 1/77* (2021.05); *A61B 5/031* (2013.01); *A61B 2017/22084* (2013.01);
(Continued)

(58) Field of Classification Search
CPC .... A61M 2209/082; A61M 1/85; A61M 1/77; A61M 1/772; A61M 2205/3344;
(Continued)

(56) References Cited

U.S. PATENT DOCUMENTS 4,026,276 A * 5/1977 Chubbuck ............. G01L 19/086
600/407
4,156,422 A * 5/1979 Hildebrandt ........ A61M 27/006
604/9

(Continued)

FOREIGN PATENT DOCUMENTS

CN 1198683 A 11/1998
CN 106344976 A * 1/2017 .......... A61M 1/0001
(Continued)

*Primary Examiner* — Scott J Medway
(74) *Attorney, Agent, or Firm* — The Webb Law Firm

(57) ABSTRACT

A fluid exchange system may include a control unit comprising a processor; a tube set attachment removably connected to the control unit, the tube set attachment comprising a tube set fluidly connected to a fluid source and a drainage receptacle; a catheter fluidly connected to the tube set; and at least one sensor positioned on at least one of the control unit and the tube set attachment, wherein the control unit may be configured to supply fluid to a patient through the tube set and drain fluid from the patient via the tube set, and wherein the control unit may be configured to receive measurements from the at least one sensor to adjust the supply of the fluid to the patient and the drainage of the fluid from the patient.

22 Claims, 20 Drawing Sheets

(52) U.S. Cl.
CPC .............. *A61B 2217/005* (2013.01); *A61M 2205/3331* (2013.01); *A61M 2210/0693* (2013.01)

(58) Field of Classification Search
CPC .. A61M 2205/3351; A61M 2205/3355; A61M 2025/0003; A61M 27/006; A61M 2210/0693; A61M 2230/005; A61M 2202/0464; A61M 2205/3334; A61B 1/015
See application file for complete search history.

(56) References Cited

U.S. PATENT DOCUMENTS

| | | | | |
|---|---|---|---|---|
| 4,206,762 | A * | 6/1980 | Cosman | A61B 5/0031 73/717 |
| 4,342,218 | A * | 8/1982 | Fox | A61B 5/02156 73/1.62 |
| 4,621,647 | A * | 11/1986 | Loveland | A61B 5/031 600/487 |
| 4,776,840 | A * | 10/1988 | Freitas | A61M 3/0262 604/38 |
| 4,884,065 | A * | 11/1989 | Crouse | A61M 5/365 250/573 |
| 5,460,490 | A | 10/1995 | Carr et al. | |
| 5,514,088 | A | 5/1996 | Zakko | |
| 5,607,391 | A * | 3/1997 | Klinger | A61B 17/0218 604/35 |
| 5,954,691 | A | 9/1999 | Prosl | |
| 6,248,080 | B1 * | 6/2001 | Miesel | A61B 5/0215 600/311 |
| 6,537,232 | B1 * | 3/2003 | Kucharczyk | A61M 31/005 600/561 |
| 8,398,581 | B2 | 3/2013 | Panotopoulos | |
| 8,444,592 | B2 * | 5/2013 | Williams | A61M 5/172 604/113 |
| 8,608,716 | B2 * | 12/2013 | Holper | A61M 1/73 604/9 |
| 9,072,865 | B2 | 7/2015 | Negre et al. | |
| 9,248,221 | B2 * | 2/2016 | Look | A61M 1/74 |
| 9,517,295 | B2 * | 12/2016 | Wilt | A61M 1/1619 |
| 9,572,921 | B2 * | 2/2017 | Shener | A61M 3/0208 |
| 9,662,478 | B2 * | 5/2017 | Browd | A61M 27/006 |
| 10,369,353 | B2 * | 8/2019 | Giftakis | A61N 1/36082 |
| 10,413,710 | B2 * | 9/2019 | Lutz | A61B 5/031 |
| 10,653,442 | B2 * | 5/2020 | Anand | A61M 5/3286 |
| 11,278,657 | B2 * | 3/2022 | DePasqua | A61M 27/006 |
| 2002/0052563 | A1 * | 5/2002 | Penn | A61N 1/36557 600/561 |
| 2004/0260229 | A1 * | 12/2004 | Meir | A61B 5/031 604/9 |
| 2005/0075624 | A1 * | 4/2005 | Miesel | A61M 5/14276 604/151 |
| 2008/0319376 | A1 * | 12/2008 | Wilcox | A61M 25/003 601/2 |
| 2009/0024070 | A1 * | 1/2009 | Gelfand | A61M 1/367 604/4.01 |
| 2009/0082640 | A1 * | 3/2009 | Kovach | A61B 5/24 600/300 |
| 2010/0228179 | A1 | 9/2010 | Thomas et al. | |
| 2010/0298771 | A1 * | 11/2010 | Tan | A61M 5/44 604/113 |
| 2010/0331813 | A1 * | 12/2010 | Robinson | A61M 25/0026 604/503 |
| 2011/0275976 | A1 * | 11/2011 | Negre | G01F 1/68 604/9 |
| 2012/0078137 | A1 * | 3/2012 | Mendels | G01F 23/2924 600/584 |
| 2012/0226215 | A1 * | 9/2012 | Hsu | A61M 27/006 604/9 |
| 2012/0289895 | A1 | 11/2012 | Tsoukalis | |
| 2013/0310706 | A1 | 11/2013 | Stone et al. | |
| 2014/0371545 | A1 * | 12/2014 | Ben-Ari | A61B 5/031 600/301 |
| 2015/0224284 | A1 | 8/2015 | Panotopoulos et al. | |
| 2016/0331897 | A1 * | 11/2016 | Anand | A61M 5/1723 |
| 2016/0367747 | A1 | 12/2016 | Loske | |
| 2017/0095649 | A1 * | 4/2017 | Vase | A61F 7/123 |
| 2017/0136209 | A1 * | 5/2017 | Burnett | A61M 1/74 |
| 2017/0157374 | A1 * | 6/2017 | Hedstrom | A61M 27/006 |
| 2017/0203084 | A1 * | 7/2017 | Lad | A61M 27/006 |
| 2017/0209056 | A1 * | 7/2017 | Browd | A61B 5/032 |
| 2019/0009014 | A1 * | 1/2019 | Chen | A61M 1/14 |

FOREIGN PATENT DOCUMENTS

| | | |
|---|---|---|
| JP | H06504451 A | 5/1994 |
| JP | 2014155865 A | 8/2014 |
| JP | 2017774 A | 1/2017 |
| WO | 9112830 A1 | 9/1991 |
| WO | 2014164655 A1 | 10/2014 |

* cited by examiner

FLUID EXCHANGE SYSTEM AND RELATED METHODS

CROSS-REFERENCE TO RELATED APPLICATIONS

This application is the United States national phase of International Application No. PCT/IB2018/051838 files Mar. 19, 2018, and claims the benefit of U.S. Provisional Patent Application No. 62/473,301, filed Mar. 17, 2017 the disclosure of which is hereby incorporated by reference in its entirety. This application is also related to U.S. Provisional Patent Application No. 62/470,711, filed Mar. 13, 2017, the disclosure of which is hereby incorporated by reference in its entirety.

BACKGROUND OF THE INVENTION

Field of the Invention

The present disclosure relates generally to a fluid exchange system for medical applications and, more particularly, a fluid exchange system configured to prevent or remove blockages of a multi-lumen catheter used for targeted fluid exchange.

Description of Related Art

The present disclosure addresses a massive medical need, namely, the treatment of cerebral vasospasm following Subarachnoid Hemorrhage (SAH) due to an aneurysm's rupture or any other SAH cause. Angiographic cerebral vasospasm is seen in 30-70% of patients with aneurysmal SAH and more than one third of these patients develop clinically significant vasospasm which is the leading morbidity and mortality factor of this pathology. It is widely accepted that degradation products of blood are the causative factor of vasospasm. Since it could be determined that the amount of subarachnoid blood is correlated to the risk of vasospasm, reducing the subarachnoid clot burden at the time of surgery reduces the risk of vasospasm. It is also well known that clearing of blood from the subarachnoid cisterns during surgery helps reduce the incidence and severity of vasospasm. Here, however, it is highly difficult and invasive to clear all the blood sufficiently, since clearing the subarachnoid blood from the cisterns following aneurysm rupture remains a technical challenge.

Traditionally, neurosurgeons adopt a broad variety of irrigation methods and drains during the intra and post-operative period. The respective risks are increasing intracranial pressure (ICP), inadequate clearance, and infection. In particular, for the treatment of vasospasm, many theories have been proposed and various treatment regimens have been applied. For example, many local and systemic pharmaceutical approaches through a variety of catheters have been tried, but there is still a need for an improved system and method to clear the blood from the subarachnoid spaces efficiently and with low risk for the patient.

A variety of additional unmet needs not addressed by current fluid exchange systems include a) evacuation of hematomas from the intracranial cavity or anywhere else in the body, with or without administration of thrombolytic drugs; and b) evacuation of abscesses and infected fluid collections from the intracranial cavity or anywhere else in the body (like meningitis, peritonitis, etc.) with or without simultaneous direct administration of antibiotic solutions to the pathology. Regarding these unmet needs, previously known drainage systems fail to meet the needs cited under items (a) and (b) since they exhibit continuous blockage problems, which compromise clinical outcome and are not suited for direct drug administration. This is valid for intracranial as well as peritoneal, thoracic, orthopedic, pathological hematomas or infected fluid collections.

Further unmet needs include direct drug delivery to malignant tumors (like liver, lung, pancreas, and prostate, cancer, disseminated intraperitoneal carcinomatosis, etc.), or other non-malignant localized pathologies (like osteomyelitis, ascites, spondylitis, etc.) in the CNS and the body, in organs or cavities, in order to avoid the side effects caused by "wasted drug" (e.g. drug not reaching the therapeutic target but exerting its action on healthy tissue) when administered systematically (per os, intravenously, etc.). Existing direct drug delivery systems cannot maintain therapeutic drug concentrations for sufficient time to achieve their therapeutic goal, as any increase of the drug volume administered increases dangerously local pressure and/or general toxicity. So far, no known local drug delivery system actually addresses the clinical need of sufficient drug volume, and all of them rely on blood circulation and other patient's natural systems for the evacuation of the therapeutically inactive and harmful metabolites of the drug pathology interaction.

An additional unmet need includes peritoneal dialysis that is actually served by devices that create significant changes of intraperitoneal volume in short time and cause discomfort and pain to the patient, while not securing a stable biochemical profile of the extracellular space over time. There is a need for a milder but continuous fluid exchange system that extends the treatment time and eliminates dangerous biochemical fluctuations between treatments, without compromising a patient's mobility and quality of life.

SUMMARY OF THE INVENTION

For meeting at least the above needs, the present disclosure provides a fluid exchange system, and related methods, which includes, but is not necessarily limited to, the following components or aspects: (1) a multi-lumen catheter, namely, a catheter, also referred to as a catheter probe, including more than one lumen, such as a combination of inner and outer lumens, or the like, (2) a pump system, and (3) a tubing system.

In one aspect of the present disclosure, a fluid exchange system may include a control unit comprising a processor; a tube set attachment removably connected to the control unit, the tube set attachment comprising a tube set fluidly connected to a fluid source and a drainage receptacle; a catheter fluidly connected to the tube set; and at least one sensor positioned on at least one of the control unit and the tube set attachment, wherein the control unit may be configured to supply fluid to a patient through the tube set and drain fluid from the patient via the tube set, and wherein the control unit may be configured to receive measurements from the at least one sensor to adjust the supply of the fluid to the patient and the drainage of the fluid from the patient, wherein, in an event a difference between a first measurement and second measurement exceeds a first pressure threshold value or is less than a second pressure threshold value, the control unit is configured to issue a pressure signal output to indicate the first pressure threshold value has been exceeded or the difference between the first and second measurements is less than the second pressure threshold value.

In another aspect of the present disclosure, the at least one sensor may include a pressure sensor, and wherein the at least one sensor sends pressure measurements to the control unit. The at least one sensor may be positioned in a cassette of the tube set attachment. The at least one sensor may send intracranial pressure measurements to the control unit. The at least one sensor may include a pressure sensor, wherein the at least one sensor may be positioned in the control unit, and wherein the at least one sensor may send intracranial pressure measurements to the control unit. The control unit may be further configured to initiate the drainage of the fluid from the patient in the event the difference between the first and second measurements from the at least one sensor exceeds the first pressure threshold value. The control unit may be further configured to initiate infusion of the fluid into the patient in the event the difference between the first and second measurements from the at least one sensor falls below the second threshold value. The fluid may be a pharmaceutical drug or therapeutic agent. The measurements received from the at least one sensor may be intracranial pressures. The catheter may include a first lumen including a proximal end and a distal end; and a second lumen disposed within the first lumen and including a proximal end and a distal end; a valve disposed within at least one of the first lumen and the second lumen and configured to control a flow of fluid through the catheter; and a sleeve provided on the distal ends of the first and second lumens. At least one aperture may be defined in at least one of the first lumen and the second lumen, wherein the sleeve may be axially displaceable relative to the first lumen and the second lumen, and wherein the sleeve may be moveable between a first position in which the at least one aperture is covered by the sleeve and a second position in which the at least one aperture is not covered by the sleeve. At least one aperture may be defined in at least one of the first lumen and the second lumen, wherein the sleeve may be rotationally displaceable relative to the first lumen and the second lumen, and wherein the sleeve may be moveable between a first position in which the at least one aperture is covered by the sleeve and a second position in which the at least one aperture is not covered by the sleeve. At least one aperture may be defined in at least one of the first lumen and the second lumen, wherein the sleeve may be rotationally displaceable relative to the first lumen and the second lumen, and wherein the sleeve may be moveable between a first position in which the at least one aperture is covered by the sleeve and a second position in which the at least one aperture is not covered by the sleeve. The tube set attachment may include a cassette configured to removably connect the tube set attachment to the control unit. The control unit may include a pump to supply fluid from the fluid source to the patient via the tube set. The tube set may include a first tube fluidly connected to the fluid source at a first end and the catheter at a second end, and a second tube fluidly connected to the catheter at a first end and the drainage receptacle at a second end. The fluid source may include an infusion bag. The drainage receptacle may include an aspiration bag. The drainage receptacle may be connected to the control unit via a graduated measuring band. The drainage receptacle may be adjustable in a vertical direction relative to the control unit. The tube set attachment may include at least one pressure sensor to measure a pressure of the fluid flowing through the tube set. The tube set attachment may be disposable. The tube set attachment may include a security valve positioned between a portion of the tube set and a cassette fluidly connected to the tube set. The control unit may include a graphical user interface comprising at least a flow rate indicator and an intracranial pressure alarm that monitors intracranial pressure levels in a patient connected to the fluid exchange system. The intracranial pressure alarm may include a high intracranial pressure threshold alarm and a low intracranial pressure threshold alarm. The control unit may include an air sensor connected to a portion of the tube set to identify when the fluid source is empty.

In another aspect of the present disclosure, a computer-implemented method of monitoring an intracranial pressure using a fluid exchange system, the method may include receiving, at a processor, a first pressure value in an intracranial cavity; infusing a liquid into the intracranial cavity; receiving, at the processor, a second pressure value of the intracranial cavity; computing, using the processor, a difference between the first and second intracranial pressures; and in an event the difference between the first and second intracranial pressures exceeds a first pressure threshold value or is less than a second pressure threshold value, issuing a pressure signal output, via the processor, to indicate the first pressure threshold value has been exceeded or the difference between the first and second intracranial pressures is less than the second pressure threshold value.

In another aspect of the present disclosure, the processor may determine a first temporal progression curve of pressure corresponding to the first measured pressure valve, and wherein, the processor determines a second temporal progression curve of pressure corresponding to the second measured pressure valve. The method may further include computing, via the processor, a first derivative function from the first measured pressure valve and a second derivative function from the second measured pressure value. The method may further include determining, via the processor, a first maximum slope value of the first derivative function and a second maximum slope value of the second derivative function. The method may further include computing, via the processor, a difference between the first maximum slope value and the second maximum slope value; and in an event the difference between the first and second maximum slope values exceeds the first pressure threshold value or is less than the second pressure threshold value, issuing a pressure signal output, via the processor, to indicate the pressure threshold value has been exceeded or the difference between the first and second maximum slope values is less than the second pressure threshold value. The method may further include, in the event the first pressure threshold value has been exceeded, operating, the fluid exchange system via the processor to aspirate fluid from the intracranial cavity to reduce the intracranial pressure. The method may further include in the event the difference between the first and second intracranial pressures is less than the second pressure threshold value, operating the fluid exchange system via the processor to infuse additional fluid into the intracranial cavity to increase the intracranial pressure.

In another aspect of the present disclosure, a catheter for a fluid exchange system, may include a lumen comprising a proximal end and a distal end and a lumen wall extending between the proximal end and the distal end, wherein the lumen wall defines an interior lumen space; at least one aperture defining a passage through the lumen wall and into the interior lumen space; and a movable sleeve covering at least a portion of the lumen wall, wherein the sleeve is moveable relative to the lumen wall between a first position in which the sleeve covers a first amount of the at least one aperture and a second position in which the sleeve covers a second amount of the at least one aperture, wherein the second amount is greater than the first amount.

In another aspect of the present disclosure, the sleeve may be axially displaceable relative to the lumen wall between the first position and the second position. The sleeve may include a sleeve shoulder that is at least partially disposed within one of the at least one aperture, wherein axial displacement of the sleeve relative to the lumen wall between the first position and the second position may cause the sleeve shoulder to slide within the one of the at least one aperture so as to clear debris from the one of the at least one aperture. The sleeve may include a plurality of sleeve shoulders and the catheter may include a plurality of apertures each defining a passage through the lumen wall and into the interior lumen space, wherein each of the sleeve shoulders may be at least partially disposed in one of the plurality of apertures, and wherein axial displacement of the sleeve relative to the lumen wall between the first position and the second position may cause each of the sleeve shoulders to slide within the one of the plurality of apertures so as to clear debris from the one of the plurality of apertures. The sleeve may be rotatable relative to the lumen wall between the first position and the second position. The sleeve may include at least one sleeve element, and wherein rotation of the sleeve relative to the lumen wall may cause the at least one sleeve element to pass over the at least one aperture so as to clear debris from the at least one aperture. The sleeve may include a plurality of sleeve elements and a plurality of apertures each defining a passage through the lumen wall and into the interior lumen space, and wherein rotation of the sleeve relative to the lumen wall may cause the plurality of sleeve extensions to pass over the plurality of apertures so as to clear debris from the plurality of apertures. The first amount may be equal to none of the at least one aperture. The catheter may include a second lumen disposed within the interior lumen space.

In another aspect of the present disclosure, a catheter for a fluid exchange system, may include a first lumen comprising a proximal end and a distal end and a lumen wall extending between the proximal end and the distal end, wherein the lumen wall defines a first interior lumen space; at least one aperture defining a passage through the lumen wall of the first lumen and into the first interior lumen space; and a second lumen comprising a proximal end and a distal end and a lumen wall extending between the proximal end and the distal end and defining a second interior lumen space, wherein the second lumen may be disposed within the first interior lumen space and the lumen wall of the second lumen separates the first interior lumen space from the second interior lumen space; and a valve disposed in the lumen wall of the second lumen, wherein the valve is adapted to use fluid flow through the second interior lumen space to restrict fluid flow through the first interior lumen space.

In another aspect of the present disclosure, the first lumen may be connected to an aspiration device adapted to aspirate an aspiration fluid through the first interior lumen space, wherein the second lumen may be connected to an infusion device adapted to infuse an infusion fluid through the second interior lumen space, wherein the valve may be an opening in the lumen wall of the second lumen, wherein the opening may be positioned proximal to the at least one aperture, and wherein a flow of a portion of the infusion fluid through the opening from the second interior lumen space into the first interior lumen space may restrict flow of the aspiration fluid through the first interior lumen space. The first lumen may be connected to an aspiration device adapted to aspirate an aspiration fluid through the first interior lumen space, wherein the second lumen may be connected to an infusion device adapted to infuse an infusion fluid through the second interior lumen space, wherein the valve may be an opening in the lumen wall of the second lumen, wherein the opening may be positioned proximal to the at least one aperture, and wherein a flow of a portion of the infusion fluid through the opening from the second interior lumen space into the first interior lumen space may restrict flow of the aspiration fluid through the first interior lumen space. The valve may include an expandable balloon valve, wherein fluid flow through the second interior lumen space may cause the balloon valve to expand into the first interior lumen space, thereby restricting flow through the first interior lumen space. The balloon valve may have a porous surface through which a fluid flowing through the second interior space can enter the first interior lumen space. The second lumen may include a check valve to restrict flow through the second lumen, wherein the check valve may be located between the proximal end of the second lumen and the balloon valve. The valve may include at least one leaflet, wherein fluid flow through the second interior lumen space may cause the at least one leaflet to extend into the first interior lumen space, thereby restricting flow through the first interior lumen space. The valve may include a plurality of leaflets, wherein fluid flow through the second interior lumen space may cause each of the plurality of leaflets to extend into the first interior lumen space, thereby restricting flow through the first interior lumen space. The at least one leaflet may be porous such that a fluid can flow through the leaflet in a thickness direction.

In another aspect of the present disclosure, a method of delivering a drug to a patient, may include activating a control unit in a fluid exchange system as recited above; infusing the drug to the patient via the tubing set and catheter of the fluid exchange system; monitoring the measurements received from the at least sensor; and in the event the measurements exceed a high threshold value, draining fluid from the patient via the catheter and tubing set. The drug may include a pharmaceutical drug or therapeutic agent.

The present invention is also disclosed in the following clauses.

Clause 1: A fluid exchange system, comprising: a control unit comprising a processor; a tube set attachment removably connected to the control unit, the tube set attachment comprising a tube set fluidly connected to a fluid source and a drainage receptacle; a catheter fluidly connected to the tube set; and at least one sensor positioned on at least one of the control unit and the tube set attachment, wherein the control unit is configured to supply fluid to a patient through the tube set and drain fluid from the patient via the tube set, and wherein the control unit is configured to receive measurements from the at least one sensor to adjust the supply of the fluid to the patient and the drainage of the fluid from the patient, wherein, in an event a difference between a first measurement and second measurement exceeds a first pressure threshold value or is less than a second pressure threshold value, the control unit is configured to issue a pressure signal output to indicate the first pressure threshold value has been exceeded or the difference between the first and second measurements is less than the second pressure threshold value.

Clause 2: The fluid exchange system as recited in Clause 1, wherein the at least one sensor comprises a pressure sensor, and wherein the at least one sensor sends pressure measurements to the control unit.

Clause 3: The fluid exchange system as recited in Clause 2, wherein the at least one sensor is positioned in a cassette of the tube set attachment.

Clause 4: The fluid exchange system as recited in Clause 2 or Clause 3, wherein the at least one sensor sends intracranial pressure measurements to the control unit.

Clause 5: The fluid exchange system as recited in any of Clauses 1-4, wherein the at least one sensor comprises a pressure sensor, wherein the at least one sensor is positioned in the control unit, and wherein the at least one sensor sends intracranial pressure measurements to the control unit.

Clause 6: The fluid exchange system as recited in any of Clauses 1-5, wherein, the control unit is further configured to initiate the drainage of the fluid from the patient in the event the difference between the first and second measurements from the at least one sensor exceeds the first pressure threshold value.

Clause 7: The fluid exchange system as recited in any of Clauses 1-6, wherein, the control unit is further configured to initiate infusion of the fluid into the patient in the event the difference between the first and second measurements from the at least one sensor falls below the second threshold value.

Clause 8: The fluid exchange system as recited in any of Clauses 1-7, wherein the fluid comprises a pharmaceutical drug or therapeutic agent.

Clause 9: The fluid exchange system as recited in any of Clauses 1-8, wherein the measurements received from the at least one sensor comprise intracranial pressures.

Clause 10: The fluid exchange system as recited in any of Clauses 1-9, wherein the catheter comprises: a first lumen comprising a proximal end and a distal end; and a second lumen disposed within the first lumen and comprising a proximal end and a distal end; a valve disposed within at least one of the first lumen and the second lumen and configured to control a flow of fluid through the catheter; and a sleeve provided on the distal ends of the first and second lumens.

Clause 11: The fluid exchange system as recited in Clause 10, wherein at least one aperture is defined in at least one of the first lumen and the second lumen, wherein the sleeve is axially displaceable relative to the first lumen and the second lumen, and wherein the sleeve is moveable between a first position in which the at least one aperture is covered by the sleeve and a second position in which the at least one aperture is not covered by the sleeve.

Clause 12: The fluid exchange system as recited in Clause 10 or Clause 11, wherein at least one aperture is defined in at least one of the first lumen and the second lumen, wherein the sleeve is rotationally displaceable relative to the first lumen and the second lumen, and wherein the sleeve is moveable between a first position in which the at least one aperture is covered by the sleeve and a second position in which the at least one aperture is not covered by the sleeve.

Clause 13: The fluid exchange system as recited in any of Clauses 1-12, wherein the tube set attachment further comprises a cassette configured to removably connect the tube set attachment to the control unit.

Clause 14: The fluid exchange system as recited in any of Clauses 1-13, wherein the control unit further comprises a pump to supply fluid from the fluid source to the patient via the tube set.

Clause 15: The fluid exchange system as recited in any of Clauses 1-14, wherein the tube set comprises a first tube fluidly connected to the fluid source at a first end and the catheter at a second end, and a second tube fluidly connected to the catheter at a first end and the drainage receptacle at a second end.

Clause 16: The fluid exchange system as recited in any of Clauses 1-15, wherein the fluid source comprises an infusion bag.

Clause 17: The fluid exchange system as recited in any of Clauses 1-16, wherein the drainage receptacle comprises an aspiration bag.

Clause 18: The fluid exchange system as recited in any of Clauses 1-17, wherein the drainage receptacle is connected to the control unit via a graduated measuring band.

Clause 19: The fluid exchange system as recited in any of Clauses 1-18, wherein the drainage receptacle is adjustable in a vertical direction relative to the control unit.

Clause 20: The fluid exchange system as recited in any of Clauses 1-19, wherein the tube set attachment further comprises at least one pressure sensor to measure a pressure of the fluid flowing through the tube set.

Clause 21: The fluid exchange system as recited in any of Clauses 1-20, wherein the tube set attachment is disposable.

Clause 22: The fluid exchange system as recited in any of Clauses 1-21, wherein the tube set attachment includes a security valve positioned between a portion of the tube set and a cassette fluidly connected to the tube set.

Clause 23: The fluid exchange system as recited in any of Clauses 1-22, wherein the control unit further comprises a graphical user interface comprising at least a flow rate indicator and an intracranial pressure alarm that monitors intracranial pressure levels in a patient connected to the fluid exchange system.

Clause 24: The fluid exchange system as recited in Clause 23, wherein the intracranial pressure alarm includes a high intracranial pressure threshold alarm and a low intracranial pressure threshold alarm.

Clause 25: The fluid exchange system as recited in any of Clauses 1-24, wherein the control unit further comprises an air sensor connected to a portion of the tube set to identify when the fluid source is empty.

Clause 26: A computer-implemented method of monitoring an intracranial pressure using a fluid exchange system, the method comprising: receiving, at a processor, a first pressure value in an intracranial cavity; infusing a liquid into the intracranial cavity; receiving, at the processor, a second pressure value of the intracranial cavity; computing, using the processor, a difference between the first and second intracranial pressures; and in an event the difference between the first and second intracranial pressures exceeds a first pressure threshold value or is less than a second pressure threshold value, issuing a pressure signal output, via the processor, to indicate the first pressure threshold value has been exceeded or the difference between the first and second intracranial pressures is less than the second pressure threshold value.

Clause 27: The computer-implemented method as recited in Clause 26, wherein, the processor determines a first temporal progression curve of pressure corresponding to the first measured pressure valve, and wherein, the processor determines a second temporal progression curve of pressure corresponding to the second measured pressure valve.

Clause 28: The computer-implemented method as recited in Clause 26 or 27, further comprising, computing, via the processor, a first derivative function from the first measured pressure valve and a second derivative function from the second measured pressure value.

Clause 29: The computer-implemented method as recited in Clause 28, further comprising, determining, via the processor, a first maximum slope value of the first derivative function and a second maximum slope value of the second derivative function.

Clause 30: The computer-implemented method as recited in Clause 29, further comprising: computing, via the processor, a difference between the first maximum slope value and the second maximum slope value; and in an event the difference between the first and second maximum slope values exceeds the first pressure threshold value or is less than the second pressure threshold value, issuing a pressure signal output, via the processor, to indicate the pressure threshold value has been exceeded or the difference between the first and second maximum slope values is less than the second pressure threshold value.

Clause 31: The computer-implemented method as recited in any of Clauses 26-30, further comprising, in the event the first pressure threshold value has been exceeded, operating, the fluid exchange system via the processor to aspirate fluid from the intracranial cavity to reduce the intracranial pressure.

Clause 32: The computer-implemented method as recited in any of Clauses 26-31, further comprising, in the event the difference between the first and second intracranial pressures is less than the second pressure threshold value, operating the fluid exchange system via the processor to infuse additional fluid into the intracranial cavity to increase the intracranial pressure.

Clause 33: A catheter for a fluid exchange system, comprising: a lumen comprising a proximal end and a distal end and a lumen wall extending between the proximal end and the distal end, wherein the lumen wall defines an interior lumen space; at least one aperture defining a passage through the lumen wall and into the interior lumen space; and a movable sleeve covering at least a portion of the lumen wall, wherein the sleeve is moveable relative to the lumen wall between a first position in which the sleeve covers a first amount of the at least one aperture and a second position in which the sleeve covers a second amount of the at least one aperture, wherein the second amount is greater than the first amount.

Clause 34: The catheter as recited in Clause 33, wherein the sleeve is axially displaceable relative to the lumen wall between the first position and the second position.

Clause 35: The catheter as recited in Clause 34, wherein the sleeve further comprises a sleeve shoulder that is at least partially disposed within one of the at least one aperture, wherein axial displacement of the sleeve relative to the lumen wall between the first position and the second position causes the sleeve shoulder to slide within the one of the at least one aperture so as to clear debris from the one of the at least one aperture.

Clause 36: The catheter as recited in Clause 35, wherein the sleeve comprises a plurality of sleeve shoulders and the catheter comprises a plurality of apertures each defining a passage through the lumen wall and into the interior lumen space, wherein each of the sleeve shoulders is at least partially disposed in one of the plurality of apertures, and wherein axial displacement of the sleeve relative to the lumen wall between the first position and the second position causes each of the sleeve shoulders to slide within the one of the plurality of apertures so as to clear debris from the one of the plurality of apertures.

Clause 37: The catheter as recited in any of Clauses 33-36, wherein the sleeve is rotatable relative to the lumen wall between the first position and the second position.

Clause 38: The catheter as recited in Clause 37, wherein the sleeve comprises at least one sleeve element, and wherein rotation of the sleeve relative to the lumen wall causes the at least one sleeve element to pass over the at least one aperture so as to clear debris from the at least one aperture.

Clause 39: The catheter as recited in Clause 38, wherein the sleeve comprises a plurality of sleeve elements and a plurality of apertures each defining a passage through the lumen wall and into the interior lumen space, and wherein rotation of the sleeve relative to the lumen wall causes the plurality of sleeve extensions to pass over the plurality of apertures so as to clear debris from the plurality of apertures.

Clause 40: The catheter as recited in any of Clauses 37-39, wherein the first amount is equal to none of the at least one aperture.

Clause 41: The catheter as recited in any of Clauses 33-40, wherein the catheter further comprises a second lumen disposed within the interior lumen space.

Clause 42: A catheter for a fluid exchange system, comprising: a first lumen comprising a proximal end and a distal end and a lumen wall extending between the proximal end and the distal end, wherein the lumen wall defines a first interior lumen space; at least one aperture defining a passage through the lumen wall of the first lumen and into the first interior lumen space; and a second lumen comprising a proximal end and a distal end and a lumen wall extending between the proximal end and the distal end and defining a second interior lumen space, wherein the second lumen is disposed within the first interior lumen space and the lumen wall of the second lumen separates the first interior lumen space from the second interior lumen space; and a valve disposed in the lumen wall of the second lumen, wherein the valve is adapted to use fluid flow through the second interior lumen space to restrict fluid flow through the first interior lumen space.

Clause 43: The catheter as recited in Clause 42, wherein the first lumen is connected to an aspiration device adapted to aspirate an aspiration fluid through the first interior lumen space, wherein the second lumen is connected to an infusion device adapted to infuse an infusion fluid through the second interior lumen space, wherein the valve is an opening in the lumen wall of the second lumen, wherein the opening is positioned proximal to the at least one aperture, and wherein a flow of a portion of the infusion fluid through the opening from the second interior lumen space into the first interior lumen space restricts flow of the aspiration fluid through the first interior lumen space.

Clause 44: The catheter as recited in Clause 42 or 43, wherein the valve comprises an expandable balloon valve, wherein fluid flow through the second interior lumen space causes the balloon valve to expand into the first interior lumen space, thereby restricting flow through the first interior lumen space.

Clause 45: The catheter as recited in Clause 44, wherein the balloon valve has a porous surface through which a fluid flowing through the second interior space can enter the first interior lumen space.

Clause 46: The catheter of Clause 45, wherein the second lumen comprises a check valve to restrict flow through the second lumen, wherein the check valve is located between the proximal end of the second lumen and the balloon valve.

Clause 47: The catheter as recited in any of Clauses 42-46, wherein the valve comprises at least one leaflet, wherein fluid flow through the second interior lumen space causes the at least one leaflet to extend into the first interior lumen space, thereby restricting flow through the first interior lumen space.

Clause 48: The catheter as recited in Clause 47, wherein the valve comprises a plurality of leaflets, wherein fluid flow through the second interior lumen space causes each of the plurality of leaflets to extend into the first interior lumen space, thereby restricting flow through the first interior lumen space.

Clause 49: The catheter as recited in Clause 47 or 48, wherein the at least one leaflet is porous such that a fluid can flow through the leaflet in a thickness direction.

Clause 50: A method of delivering a drug to a patient, comprising: activating a control unit in a fluid exchange system as recited in claim 1; infusing the drug to the patient via the tubing set and catheter of the fluid exchange system; monitoring the measurements received from the at least sensor; and in the event the measurements exceed a high threshold value, draining fluid from the patient via the catheter and tubing set.

Clause 51: The method as recited in Clause 50, wherein the drug comprises a pharmaceutical drug or therapeutic agent.

These and other features and characteristics of the fluid exchange system, as well as the methods of operation and functions of the related elements of the fluid exchange system, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and claims, the singular form of "a", "an", and "the" include plural referents unless the context clearly dictates otherwise.

DESCRIPTION OF THE INVENTION

Figure 1:
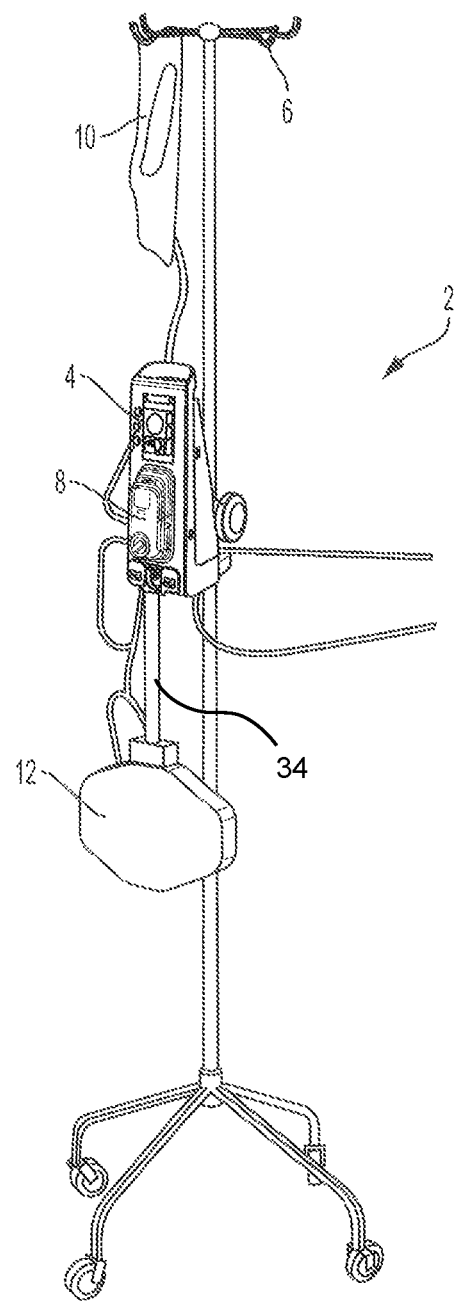
FIG. 1 is a perspective view of a fluid exchange system according to an aspect of the present disclosure.

For purposes of the description hereinafter, the terms "upper", "lower", "right", "left", "vertical", "horizontal", "top", "bottom", "lateral", "longitudinal", and derivatives thereof, shall relate to the disclosed apparatus as it is oriented in the figures. However, it is to be understood that the apparatus of the present disclosure may assume alternative variations and step sequences, except where expressly specified to the contrary. It is also to be understood that the specific systems and processes illustrated in the attached drawings, and described in the following specification, are simply exemplary examples of the apparatus disclosed herein. Hence, specific dimensions and other physical characteristics related to the examples disclosed herein are not to be considered as limiting.

As used herein, the terms "communication" and "communicate" refer to the receipt, transmission, or transfer of one or more signals, messages, commands, or other types of data. For one unit or device to be in communication with another unit or device means that the one unit or device is able to receive data from and/or transmit data to the other unit or device. A communication may use a direct or indirect connection, and may be wired and/or wireless in nature. Additionally, two units or devices may be in communication with each other even though the data transmitted may be modified, encrypted, processed, routed, etc., between the first and second unit or device. It will be appreciated that numerous arrangements are possible. Any known electronic communication protocols and/or algorithms may be used such as, for example, UDP, TCP/IP (including HTTP and other protocols), WLAN (including 802.11 and other radio frequency-based protocols and methods), analog transmissions, cellular networks, and/or the like.

Referring to the drawings in which like reference numerals refer to like parts throughout the several views thereof, the present disclosure is generally directed to a fluid exchange system for medical applications and, more particularly, a fluid exchange system configured to prevent or remove blockages of a multi-lumen catheter used for targeted fluid exchange.

With reference to FIG. 1, a fluid exchange system 2 (hereinafter "system 2") according to the present disclosure is shown and described. In one aspect, the system 2 is an intracranial pressure (ICP) drainage system intended for use by professional medical personnel and those experienced in neurological/neurosurgical medical care. By using the system 2, ICP of a patient is kept at a safe level by draining excessive intracranial fluid. As will be described in greater detail below, the system 2 includes, among other components, an infusion support mechanism used to flush the system 2 if occluded. The infusion support mechanism works by producing a bolus pulse using a short period of high flow (i.e., flow pulses). The system 2 is intended for stationary use at a hospital for the purpose of monitoring ICP and draining intracranial fluid in order to control the patient's ICP, facilitating diagnosis of the patient, and identifying recommended follow-up or continued treatment.

In one aspect, the system 2 includes a control unit 4 connected to an IV pole 6 or other support structure, a tube set attachment 8, a fluid source 10, and a drainage receptacle 12. The IV pole 6 may include a plurality of wheels provided on a bottom end thereof to enable medical personnel to move the system 2. An upper end of the IV pole 6 may include at least one hook to hold the fluid source 10. The control unit 4, the drainage receptacle 12, and the fluid source 10 may be connected to the IV pole 6 using any suitable connection means for securing the control unit 4 and the drainage receptacle 12 to the IV pole 6. The fluid source 10 and the drainage receptacle 12 are fluidly connected to the tube set attachment 8. In one aspect, the fluid source 10 is an infusion bag. In one aspect, the drainage receptacle 12 is an aspiration bag. The fluid source 10 can be positioned above the tube set attachment 8 and directs fluid into the tube set attachment 8. The drainage receptacle 12 can be positioned beneath the tube set attachment 8 and receives fluid drained from the patient and through the tube set attachment 8. Each of the components of the system 2 will be described in greater detail below.

Figure 2:
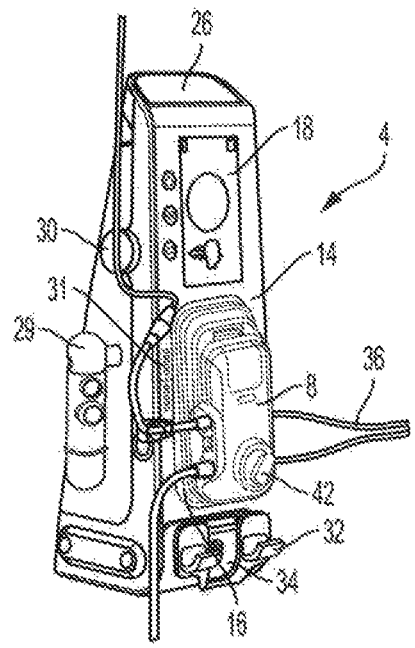
FIG. 2 is a left perspective view of a control unit of the fluid exchange system of FIG. 1.
Figure 3:
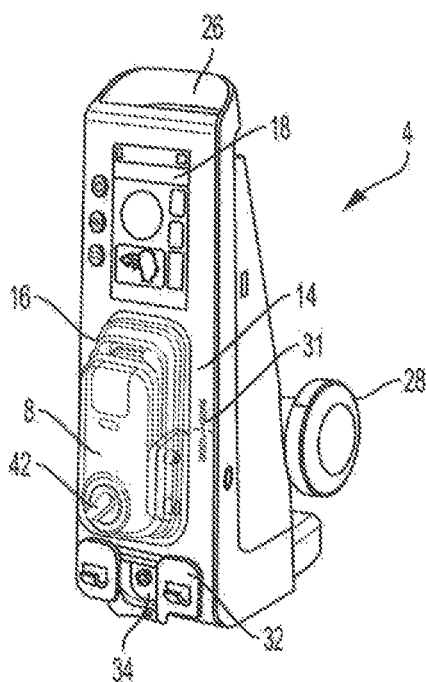
FIG. 3 is a right perspective view of the control unit of FIG. 2.
Figure 4:
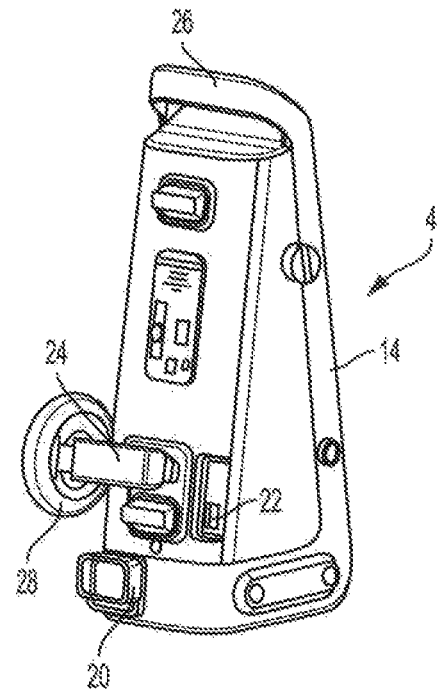
FIG. 4 is a rear view of the control unit of FIG. 2.

With reference to FIGS. 2-4, the control unit 4 of the system 2 is shown and described in greater detail. The control unit 4 may be a computer-based management system that utilizes, for example, software and/or firmware to enable pump and sensor control and appropriate delivery of the therapy fluid to the patient, body cavity or tissue of a patient. The software and/or firmware can include algorithms in the form of programming instructions stored in non-transitory, machine-readable media associated with the system 2. The programming instructions can be executed by a processor associated with the control unit 4 to enable the control unit 4 to perform the various tasks and methods discussed herein.

Figure 38:
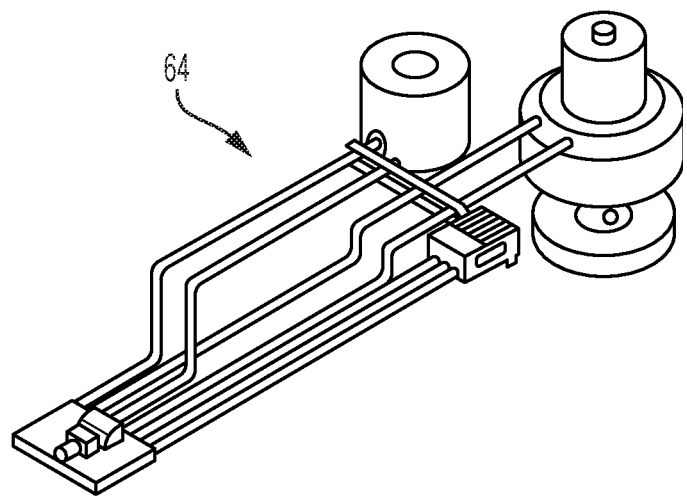
FIG. 38 is a perspective view of a pinch valve used in the control unit of the present disclosure.

The control unit 4 can include a pump 66 that is configured to direct fluid through the tube set attachment 8. The pump 66 can be configured to direct fluid from the fluid source 10 through the tube set attachment 8 to a patient. The pump 66 can also be configured to drain fluid from the patient through the tube set attachment 8 and into the drainage receptacle 12 by generating or creating a negative pressure in the tube set attachment 8. Pumps suitable for use in this disclosure are generally known. In one aspect, the pump 66 is a peristaltic pump. The control unit 4 may also include a pinch valve 64 (shown in FIG. 38) to control the flow of fluid through the tube set attachment 8. The pump 66 and pinch valve 64 can be held within a housing 14 of the control unit 4. The control unit 4 also can include a connection port 16 to receive the tube set attachment 8.

The control unit 4 can further include a graphical user interface (GUI) 18 to display control options, alarm indications, and system parameters regarding the system 2 to a patient or medical personnel. In one aspect, the GUI 18 includes an LCD touchscreen display to permit medical personnel to operate the control unit 4. The control unit 4 also includes a central processing unit (CPU) that is configured to operate the pump 66 housed within the control unit 4. The CPU can also communicate with sensors provided in the system 2 to measure and record system operating parameters and alarm indications for the control unit 4.

The system 2 may also include flow sensors, algorithms and related methods for controlling pump motor function, for example, to achieve precise control of bolus infusions, both in volume, rate, duration, post infusion pause period and pressure measurement intervals in order to deliver pharmaceutical agents, alter tissue effect and response, achieve the desired therapeutic effect, meet safety requirements, manage unclogging of a catheter 44 and tube set 36, and achieve desired flow properties. Flow sensors may be MEMS-based flow sensors or impeller driven flow meters, for example.

With reference to FIG. 4, a back panel of the control unit 4 can include a mains input 20 for a power cable, a memory socket 22 to connect a USB memory stick or other removable memory device, an IV pole clamp 24 to connect the control unit 4 to the IV pole 6, and a handle 26 for carrying and holding the control unit 4. Medical personnel can insert a USB memory stick or other removable memory device into the memory socket 22 to record data measured by the control unit 4. The memory device can be used to transfer measurement data from the control unit 4 to a separate computer for storage and importation into spreadsheet reports. A transfer log screen on the GUI 18 of the control unit 4 may allow medical personnel to select the file or files for transfer to the memory device. The IV pole clamp 24 may include a tightening knob 28 to loosen and tighten the IV pole clamp 24 to remove or secure, respectively, the control unit 4 on the IV pole 6. The control unit 4 can also include an air sensor 30 provided on one side of the housing 14. The air sensor 30 is positioned and configured to receive tubing connected to the fluid source 10. In one aspect, the air sensor 30 is a bubble detection sensor configured to identify when the fluid source 10 has been depleted. The air sensor 30 may be in communication with the CPU of the control unit 4 to measure and record information regarding the depletion of the fluid source 10. In one aspect, the air sensor 30 is configured to send signals to the CPU of the control unit 4 to indicate the fluid source 10 has been depleted and that an alarm should be issued by the control unit 4 to notify medical personnel of this condition.

With continued reference to FIG. 4, the control unit 4 can also include a drainage receptacle hanger 32 configured to hold the drainage receptacle 12. In one aspect, the drainage receptacle 12 is an aspiration bag. The drainage receptacle hanger 32 may include a graduated measuring band 34 connected at one end to the control unit 4 and at an opposing end to the drainage receptacle 12. The graduated measuring band 34 permits the drainage receptacle 12 to be vertically adjusted relative to the control unit 4. The graduated measuring band 34 can also indicate the vertical distance between the control unit 4 and the drainage receptacle 12. As the drainage receptacle 12 is vertically adjusted relative to the control unit 4, medical personnel can determine the vertical distance between the drainage receptacle 12 and the control unit 4 or, in another aspect, the vertical distance between the drainage receptacle 12 and a patient's head positioned adjacent the system 2. In one aspect, the graduated measuring band 34 includes measurements provided thereon (such as inches, centimeters, etc.) that identify a vertical distance between the drainage receptacle 12 and the control unit 4.

The location of the control unit 4, the fluid source 10, and the drainage receptacle 12 relative to the patient may play a role in achieving the desired fluid flow rates and pressures required to deliver the intended therapy. Accordingly, the control unit 4 may include methods and instrumentation enabling and facilitating positioning of the control unit 4 relative to the patient, certain patient anatomy, the user, certain instrumentation and equipment, as well as general positioning, for example, level and height. For example, the system 2 may include a leveling system 29. The leveling system 29 may be an optical laser attached to the control unit 4 and employing a counter weight to provide self-leveling. In this embodiment, the laser indicates a position of the control unit 4 relative to the patient by marking the position or height of the control unit 4 relative the intended body cavity or patient limb. Alternatively, pressure sensors or positional sensors may be included in the control unit 4 and/or along the length of the system's tube set 36 and catheter 44. These sensors can be secured (by, e.g., adhesives or sutures) on the patient's skin or anatomy at the desired anatomical level and can be used for the purpose of detecting a location or height of the system components relative to the patient and communicating with the control unit 4 to correctly manage fluid flow and detect and deliver the correct relative pressure despite a patient's movements.

Figure 5A:
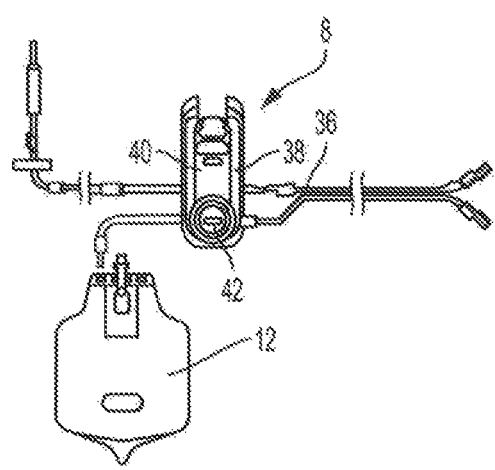
FIG. 5A is a front view of a tube set attachment of the fluid exchange system of FIG. 1.
Figure 5B:
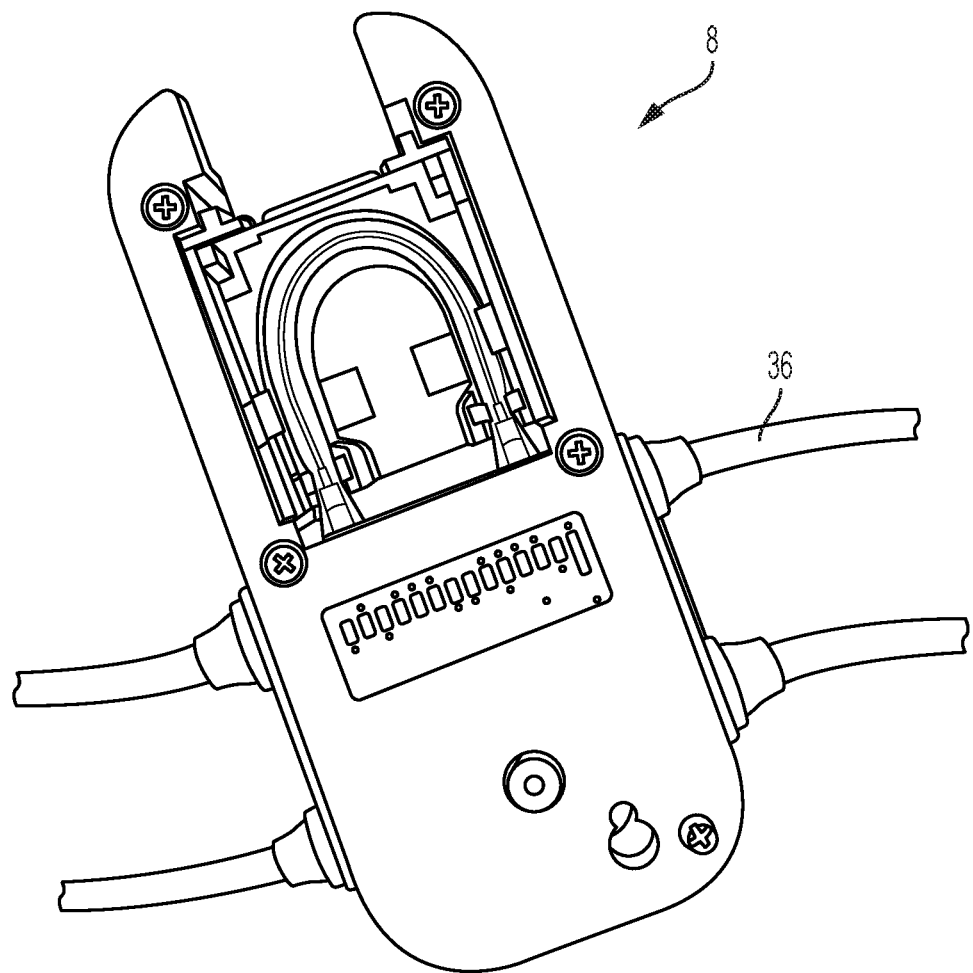
FIG. 5B is a rear view of the tube set attachment of FIG. 5A.
Figure 37:
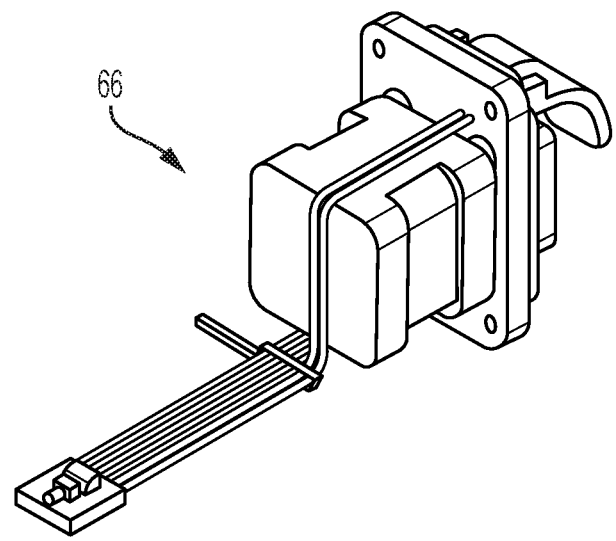
FIG. 37 is a perspective view of a pump used in the control unit of the present disclosure.
Figure 39:
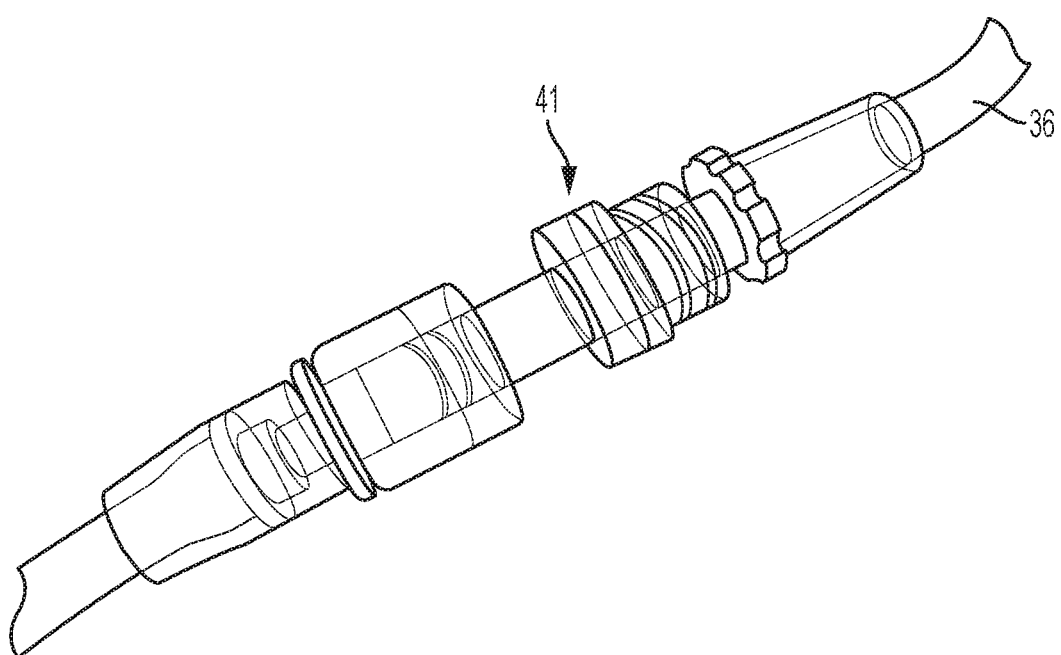
FIG. 39 is a perspective view of a security valve used in the tube set of the present disclosure.
Figure 40:
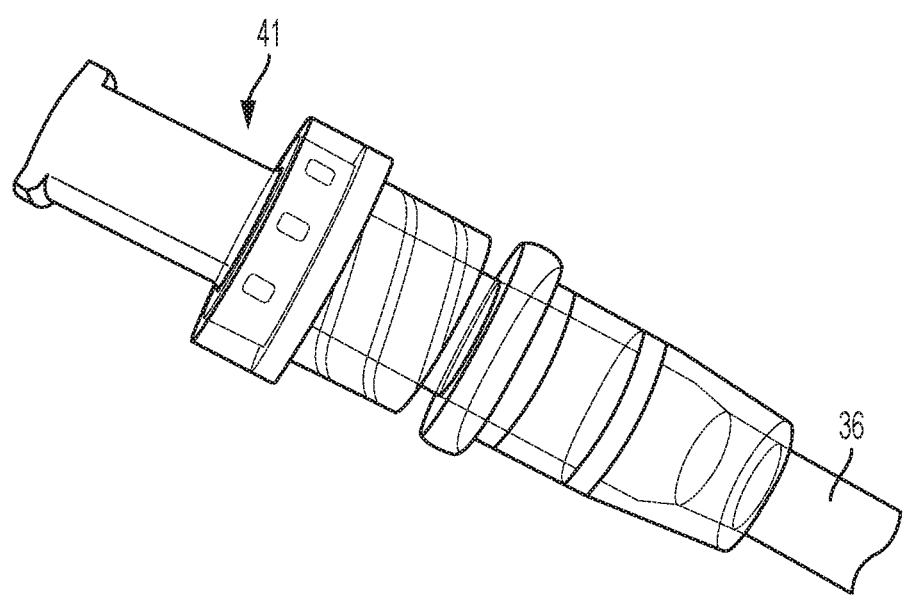
FIG. 40 is another perspective view of the security valve of FIG. 39.

With reference to FIG. 5, the tube set attachment 8 of the system 2 is shown and described in greater detail. In one aspect, the tube set attachment 8 includes a single-use, disposable, sterile tube set 36 attached to and directed through a housing 38 of the tube set attachment 8. At one end, the tube set 36 may be connected to the catheter 44 for infusion and aspiration of fluid from a patient. Details of the catheter 44 are described in greater detail below. The tube set 36 and the catheter 44 may be connected and disconnected using, for example, Luer-lock connections. The tube set attachment 8 can also include a cassette 40 that connects to the connection port 16 of the control unit 4, a pressure sensor calibration knob 42 provided on a front face thereof, and a security valve 41 (shown in FIGS. 39 and 40). The cassette 40 permits the tube set attachment 8 to be removably attached to the control unit 4. After use of the tube set attachment 8 has been completed, medical personnel can thus easily remove the tube set attachment 8 from the control unit 4 for disposal. The pressure sensor calibration knob 42 is provided on the tube set attachment 8 to calibrate and adjust pressure sensor(s) included in the tube set 36 and/or the catheter 44. Medical personnel can calibrate the pressure sensors to ensure accurate readings of fluid pressure through the tube set 36 are recorded by the pressure sensors. In one aspect, the pressure sensors are in communication with the control unit 4 to send and record pressure measurements, and, in one aspect, intracranial pressure measurements. In one aspect, the security valve 41 is positioned between a connection spike of the fluid source 10 and the cassette 40. Typically, during operation of the system 2, when the cassette 40 is mounted correctly on the control unit 4, the pump 66 in the control unit 4 (shown in FIG. 37) will close the fluid source line when not directing fluid through the tube set 36. In the event the cassette 40 is unintentionally removed from the control unit 4 while remaining connected to the patient or in the event the pump 66 begins leaking, the security valve 41 prevents a free flow of fluid from the fluid source 10 into the brain of the patient.

Figure 6:
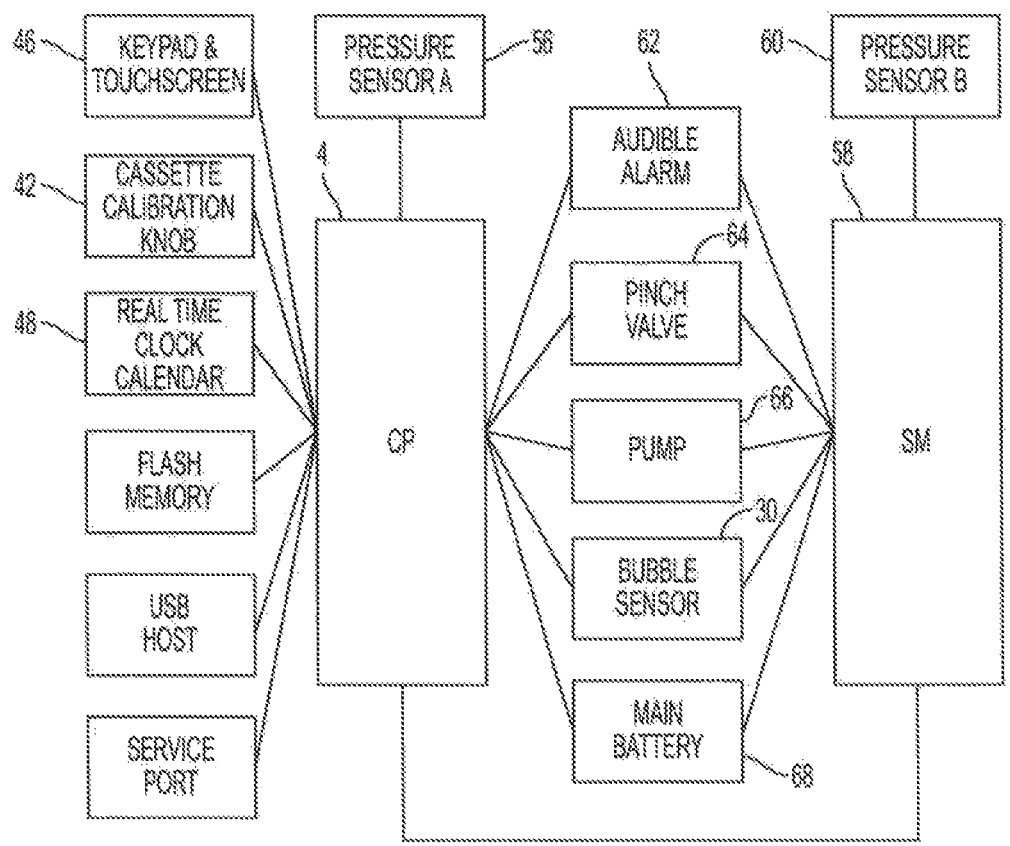
FIG. 6 is a schematic diagram of the operating system of the fluid exchange system of FIG. 1.

With reference to FIG. 6, the configuration of the operating system of the system 2 is shown and described according to one non-limiting embodiment. The control unit 4 can be in communication with various data sources, including a keypad and/or touchscreen 46 of the GUI 18, the pressure sensor calibration knob 42, a real-time clock calendar 48, a flash memory 50, a USB host 52, and a service port 54. In one aspect, the control unit 4 is also in communication with at least one pressure sensor 56 configured to record measurements of fluid pressure in the system 2. In one aspect, a pressure sensor 56 may be positioned on at least one of the following: the control unit 4, the tube set attachment 8, and the catheter 44. In another aspect, the control unit 4 is also in communication with a safety module 58. The control unit 4 may handle patient treatment, GUI 18 processing, data logging, and external communication. The safety module 58 may monitor the control unit 4 to ensure the control unit 4 is functioning as intended. The safety module 58 may be provided remotely from the control unit 4. The safety module 58 may also be in communication with a pressure sensor 60 provided on at least one of: the control unit 4, the tube set attachment 8, and the catheter 44. The control unit 4 and the safety module 58 are both in communication with an audible alarm 62, the pinch valve 64, the pump 66, the air sensor 30, and a main battery 68 that provides power to the control unit 4 and the safety module 58.

Figure 7:
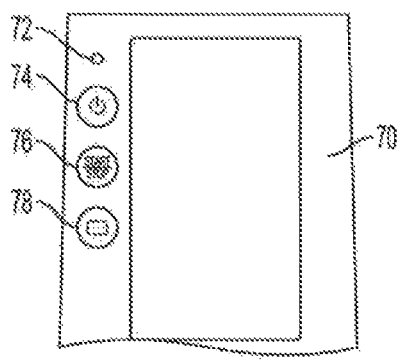
FIG. 7 is a front view of a front panel of the control unit of FIG. 2.

With reference to FIG. 7, an exemplary front panel 70 of the control unit 4 is shown and described in detail. The front panel 70 includes an LED indicator 72 that illuminates when a power connection to the control unit 4 has been established, a power button 74 to turn the control unit 4 on and off, a start/stop button 76 to initiate and terminate a treatment process conducted by the control unit 4, and a bolus button 78 to initiate a bolus process using the control unit 4.

Figure 8:
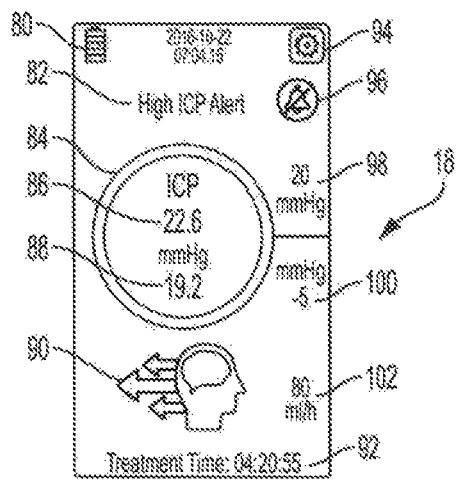
FIG. 8 is an illustration of a home screen for a graphical user interface for the control unit of FIG. 2.

With reference to FIG. 8, an exemplary embodiment of the GUI 18 of the control unit 4 is shown and described in detail. The GUI 18 may include graphical layouts for various modes of operation, arranged with appropriate order and logic to provide the desired level of user-friendliness, patient benefit, therapy protocol management, and safety. The GUI 18 provides both system performance data and patient data in text, pictorial and graphical forms to facilitate interpretation of the data and decision-making related to delivery of the therapy. Information provided to the user by this system 2 includes graphical data for therapy-related parameters, such as fluid flow through the catheter, pressures, sensor data in general as well as protocol prompts and alarms. The GUI 18 further provides information related to device setup, therapeutic protocol, safety controls, alarm and error message management, instruction to the user for device usage and delivery of therapy. The GUI 18 both enables and facilitates monitoring of patient data and status, control over and modification of therapy parameters, and user decision-making regarding delivery of appropriate therapy and patient safety.

The home screen of GUI 18 includes a battery indicator 80 to display a battery charge status and generate an alarm when the control unit 4 needs to be connected to a power source. When the treatment process can no longer be performed due to low battery power, the control unit 4 may generate an alarm with a higher intensity for a period of time, such as 3-5 minutes, to notify the medical personnel. When the battery has been depleted, the control device 4 will cease to display the ICP information and will terminate the treatment process. The home screen of GUI 18 may also include a date and time indicator 81 to present the current date and time to the medical personnel. The home screen of GUI 18 also includes an instrument status indicator 82 that displays text providing user prompts and warnings regarding the use of the system 2. In one aspect, the home screen of GUI 18 also includes an alarm state indicator 84 that displays an alarm state for medical personnel. The alarm state may include any visual indication that a certain alarm state for the system 2 has been activated. In one aspect, the alarm state may be displayed as the color red indicating a high warning, as the color yellow indicating a different level of high warning, and the color blue indicating a low-level warning. In one aspect, a grey color for the alarm state indicates there is no currently active alarm. The home screen of GUI 18 may also include an ICP indicator 86 that displays a current ICP value for a patient. The ICP value may be updated once a monitoring cycle, which can be set by medical personnel. The monitoring cycle may be every few seconds, every few minutes, or once an hour. The home screen of GUI 18 may also include a current pressure indicator 88 that displays the current ICP pressure in the patient, which is updated continuously and displayed in real-time for medical personnel to review.

Figure 9:
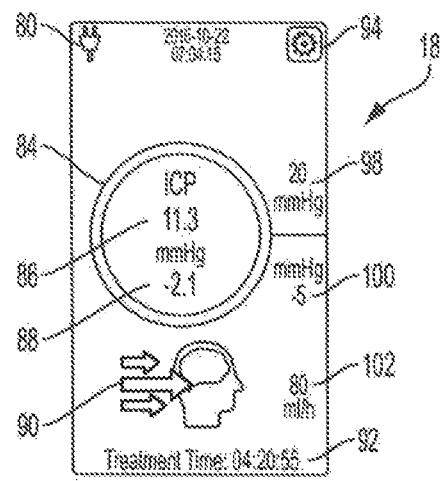
FIG. 9 is an illustration of the graphical user interface of FIG. 8 with a patient fluid flow indicator depicting an infusion process.
Figure 10:
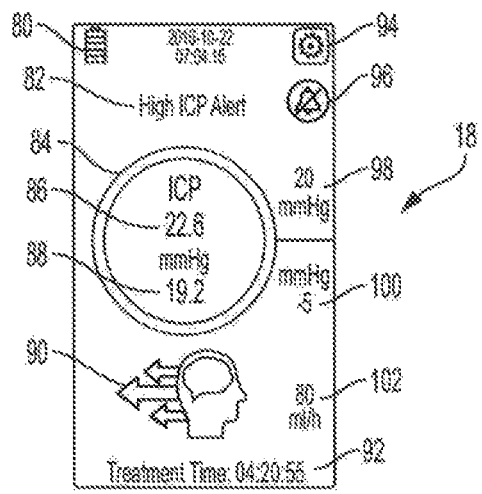
FIG. 10 is an illustration of the graphical user interface of FIG. 8 with a patient fluid flow indicator depicting an aspiration process.
Figure 11:
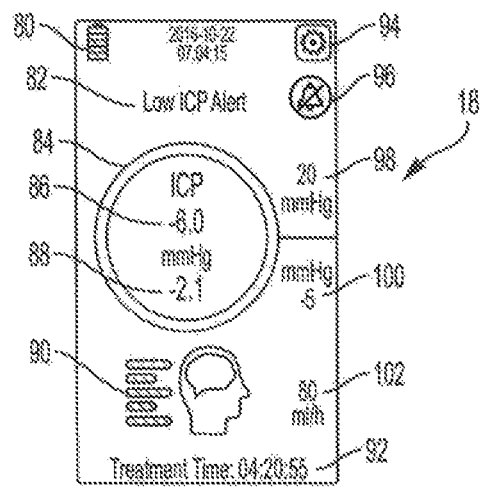
FIG. 11 is an illustration of the graphical user interface of FIG. 8 with a patient fluid flow indicator depicting a no fluid flow state.

In one aspect, the home screen of GUI 18 also includes a patient fluid flow indicator 90 that displays a flow direction of fluid relative to a patient. In one aspect, the patient fluid flow indicator 90 displays an illustration of a portion of a patient's body, such as a head, with arrows indicating a direction of fluid flow to/from the patient. In one aspect, as shown in FIG. 9, the patient fluid flow indicator 90 will display blue arrows pointed towards the illustration of the patient head to indicate that an infusion of fluid into the patient is occurring. In another aspect, as shown in FIG. 10, the patient fluid flow indicator 90 will display orange arrows pointed away from the illustration of the patient head to indicate that aspiration of the fluid from the patient's head is occurring. In another aspect, as shown in FIG. 11, the patient fluid flow indicator 90 will display green bars to indicate that no infusion or aspiration is taking place for the patient. It is to be understood that alternative colors and shapes may be used with the patient fluid flow indicator 90 to display these fluid flow states. The home screen of GUI 18 may also include a treatment time indicator 92 to display the duration of treatment for the patient.

The home screen of GUI 18 can also include a function select button 94 to allow medical personnel to select functions within the GUI 18. The home screen of GUI 18 may also include an alarm clear button 96 used by medical personnel to reset an alarm on the control unit 4. In one aspect, the home screen of GUI 18 includes indicators for displaying a high ICP alarm and low ICP alarm for medical personnel. A high ICP alarm indicator 98 is provided on the GUI 18 to indicate a high ICP setting, or limit, has been reached for the patient. The high ICP setting can be selected and adjusted by the medical personnel based on the condition of the patient. In the event the control unit 4 determines the patient's ICP has exceeded the high ICP setting, the control unit 4 may generate an alarm to alert the medical personnel, such as an audible and/or visual alarm. If the patient's ICP exceeds the high ICP setting, an aspiration process may be initiated by the control unit 4 to drain fluid from the patient's intracranial cavity. A low ICP alarm indicator 100 is also provided on the GUI 18 to indicate a low ICP setting, or limit, has been reached for the patient. The low ICP setting can be selected and adjusted by the medical personnel based on the condition of the patient. In the event the control unit 4 determines the patient's ICP has fallen below the low ICP setting, the control unit 4 may generate an alarm to alert the medical personnel, such as an audible and/or visual alarm. If the patient's ICP falls below the low ICP setting, an infusion process may be initiated by the control unit 4 to direct replacement fluid to the patient's intracranial cavity. The high and low ICP alarm indicators 98, 100 may be displayed in millimeters of mercury. The control unit 4 may have different types of alarms to indicate different ICP settings. In one aspect, the control unit 4 includes a low ICP alert that triggers an alarm when ICP is less than the low ICP setting. This alarm may be cleared when the ICP exceeds the low ICP setting. This alarm setting may include an auditory signal that beeps every twenty seconds and a visual signal on the home screen of GUI 18 including a cyan circle symbol. In one aspect, the control unit 4 includes a high ICP alert that triggers an alarm when the ICP exceeds the high ICP setting. This alarm may be cleared when the pressure drops below the high ICP setting. During the high ICP alert, aspiration and infusion are permitted by the control unit 4. This alarm setting may include an auditory signal that beeps every few seconds, such as every 5-10 seconds, such as every 7.5 seconds, and a visual signal on the home screen of GUI 18 including a yellow circle symbol. In one aspect, the control unit 4 also includes a high ICP warning that triggers an alarm when the ICP exceeds the high ICP setting by more than 3 mmHg. In this warning setting, an aspiration process will start and continue for a predetermined amount of time to drain fluid from the patient's intracranial cavity. The control unit 4 will not return to the normal treatment process until a medical personnel acknowledges the alarm by touching the home screen of GUI 18. This alarm setting may include an auditory signal that beeps every few seconds, such as every 1-4 seconds, such as every 2.5 seconds, and a visual signal on the home screen of GUI 18 including a red circle symbol.

The home screen of GUI 18 may also include a flow rate indicator 102 to display a selected flow rate of fluid to the patient. The selected flow rate may be displayed in milliliters per second. The flow rate of the fluid may be selectable and adjustable by medical personnel based on the condition of the patient.

Figure 24:
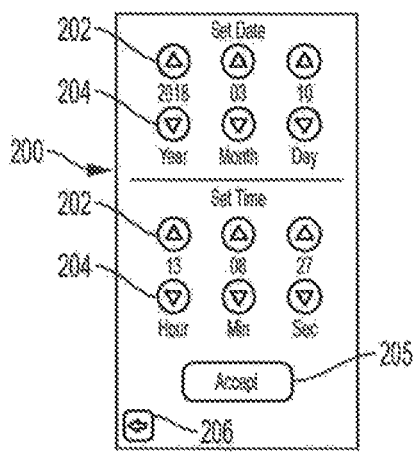
FIG. 24 is an illustration of a date and time setting screen for the GUI of the present disclosure.

FIGS. 24-35 are illustrative examples of additional screens for the GUI 18 that identify and present information to medical personnel when using the system 2. Each of these screens may be accessed either directly or indirectly through the GUI 18. As shown in FIG. 24, a date and time setting screen 200 may be accessed by pressing or selecting the date and time indicator 81 on the GUI 18. The date and time setting screen 200 presents buttons to the medical personnel to adjust and change the date and time settings for the control unit 4. In one aspect, the date and time setting screen 200 includes increase buttons 202 and decrease buttons 204 for adjusting the year, month, and/or day of the date on the control unit 4 and the hour, minute, and/or second setting for the time of the control unit 4. The increase buttons 202 may increase the value of the particular date or time setting, and the decrease buttons 204 may decrease the value of the particular date or time setting. After the date and/or time setting has been adjusted by the medical personnel, an accept button 205 may be selected to change the date and/or time settings. A return button 206 may be selected to return the control unit 4 to the GUI 18.

Figure 25:
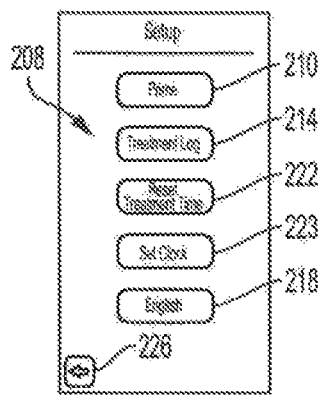
FIG. 25 is an illustration of a setup screen for the GUI for the present disclosure.

With reference to FIG. 25, a setup screen 208 is shown and described. The setup screen 208 may be accessed by selecting the function select button 94 on the GUI 18. The setup screen 208 may include several different function buttons that lead to further screens to adjust specific functions of the control unit 4. The setup screen 208 may include a prime sequence button 210 to direct the GUI 18 to a priming sequence screen 212, which will be described in greater detail below. The setup screen GUI 208 may also include a treatment log button 214 to direct the GUI 18 to a treatment log screen 216, which will be described in greater detail below. The setup screen 208 may also include a language select button 218 that directs the GUI 18 to a language select screen 220, which will be described in greater detail below. The language selection button 218 may include a label depicting the current language (e.g., English, French, Spanish, German, etc.) that is currently set for the GUI 18. The setup screen 208 may also include a reset treatment time button 222 that directs the control unit 4 to reset the amount of treatment time for the patient. The setup screen also includes a set clock button 223 that directs the GUI 18 to the date and time setting screen 200. The setup screen 208 also includes a return button 226 to return to the home screen of the GUI 18.

Figure 26:
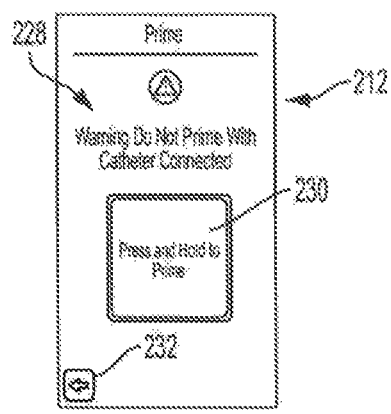
FIG. 26 is an illustration of a priming sequence screen for the GUI of the present disclosure.

With reference to FIG. 26, the priming sequence screen 212 is illustrated and described. The priming sequence screen 212 may include a warning message 228 for the medical personnel to indicate that a priming sequence should not be initiated when the catheter 44 is connected to the patient. This warning message 228 serves as a reminder to medical personnel that the catheter 44 should be disconnected from the patient before a priming sequence is initiated by the control unit 4. The priming sequence screen 212 may also include a priming sequence initiation button 230 that can be selected by the medical personnel to initiate the priming sequence for the control unit 4. In one aspect, the priming sequence initiation button 230 must be pressed and held by the medical personnel to initiate the priming sequence. In another aspect, the priming sequence initiation button 230 must only be pressed by the medical personnel to initiate the priming sequence. The priming sequence screen 212 may also include a return button 232 to return to the home screen of the GUI 18.

Figure 27:
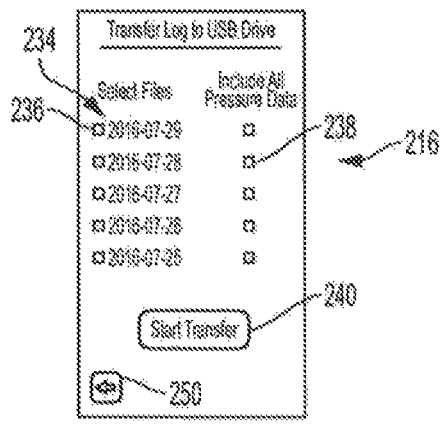
FIG. 27 is an illustration of a treatment log screen for the GUI of the present application.
Figure 28:
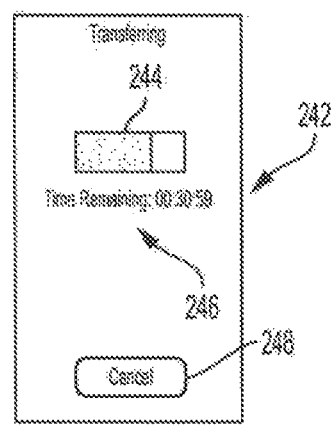
FIG. 28 is an illustration of a transfer screen for the GUI of the present disclosure.

With reference to FIG. 27, the treatment log screen 216 is illustrated and described. The treatment log screen 216 allows the medical personnel to select data files to transfer to a USB drive, a computer device connected to the control unit 4, a phone, a remote computer server, or any other type of data-receiving device. The treatment log screen 216 may include a column of treatment log files 234 identified by the specific date that the treatment log was recorded. Each specific date may include a selectable checkbox button 236 positioned adjacent to the specific date to permit the medical personnel to select the specific date of treatment log files that should be transferred. The treatment log screen 216 may also include a column of selectable checkbox buttons 238 next to each specific date to permit the medical personnel to select that all of the pressure data files for that specific be transferred. The treatment log screen 216 may also include a transfer button 240 that can be selected after the medical personnel has selected the specific pressure data or treatment log files that are to be transferred from the control unit 4. After the transfer button 240 has been selected by the medical personnel, the control unit 4 moves to a transfer screen 242, as shown in FIG. 28. The transfer screen 242 may include a rising bar indicator 244 that indicates to the medical personnel the percentage of treatment log files or pressure data that has been currently transferred. The transfer screen 242 may also include an estimated remaining time of transfer indicator 246 to indicate to the medical personnel the remaining amount of time before the treatment log files or pressure data has been fully transferred. The transfer screen 242 may also include a cancel button 248 that the medical personnel can select to cancel the transfer process of the control unit 4. Upon selection of the cancel button 248 or completion of the transfer process, the transfer screen 242 will revert back to the treatment log screen 216. The treatment log screen 216 may also include a return button 250 to return to the home screen of the GUI 18.

Figure 29:
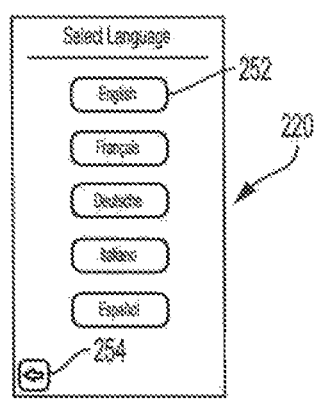
FIG. 29 is an illustration of a language select screen for the GUI of the present disclosure.

With reference to FIG. 29, the language select screen 220 is illustrated and described. The language select screen 220 may be accessed by selecting the language selection button 218 on the setup screen 208. The language select screen 220 may include several different language buttons 252. Each language button 252 may include a label depicting a different language (e.g., English, Deutsche, Francais, and Espariol, for example) that can be selected by the medical personnel. By selecting a certain language button 252, the control unit 4 will change the language displayed by the GUI 18 to correspond to the selected language. The language select screen 220 may also include a return button 254 that can be selected to return to the home screen of the GUI 18.

Figure 30:
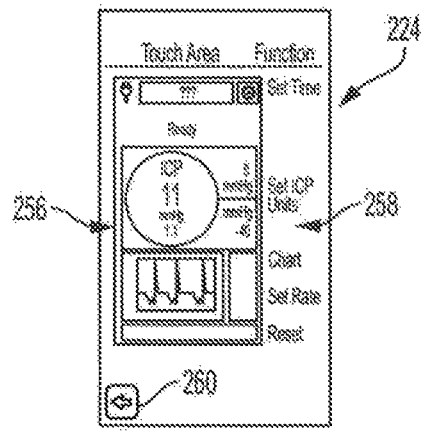
FIG. 30 is an illustration of a touchscreen help screen for the GUI of the present disclosure.
Figure 31:
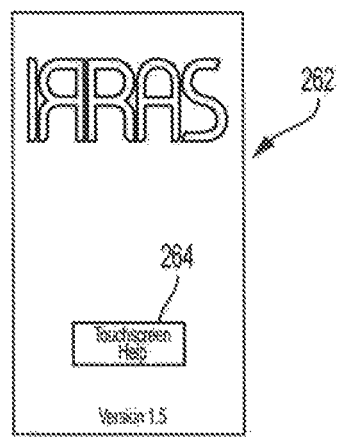
FIG. 31 is an illustration of a software version screen for the GUI of the present disclosure.

With reference to FIG. 30, the touchscreen help screen 224 is illustrated and described. The touchscreen help screen 224 may be accessed by selecting the touchscreen help button 222 on the setup screen 208. The touchscreen help screen 224 may illustrate the GUI 18 touchscreen area 256, as well as additional function buttons 258 that may be accessed by the medical personnel. The function buttons 258 may include a "set time" button, a "set ICP limits" button, a "chart" button, a "set flow rate" button, and/or a "reset" button. Therefore, instead of selecting the specific icons on the home screen of the GUI 18, the medical personnel can select one of the function buttons 258 on the touchscreen help screen 224 to access the particular screen. The touchscreen help screen 224 may also include a return button 260 to return to the home screen of the GUI 18. As shown in FIG. 31, a software version screen 262 may also include a touchscreen help button 264 that directs the GUI 18 to the touchscreen help screen 224.

Figure 32:
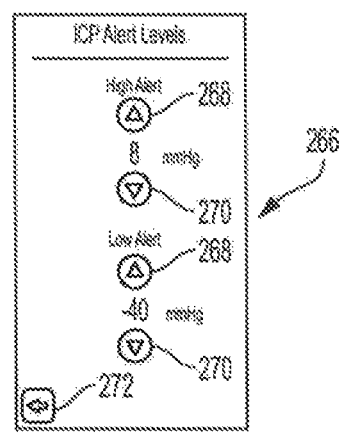
FIG. 32 is an illustration of an ICP alert level screen for the GUI of the present disclosure.

With reference to FIG. 32, an ICP alert level screen 266 is illustrated and described. The ICP alert level screen 266 may be accessed by selecting at least one of the high ICP alarm indicator 98 and the low ICP alarm indicator 100 on the GUI 18. The ICP alert level screen 266 may permit the medical personnel to adjust the high ICP level threshold and the low ICP level threshold for the system 2. The ICP alert level screen 266 may display the current setting for the high ICP level threshold and the low ICP level threshold. In one aspect, the high and low ICP level thresholds are displayed in mmHg units. The ICP alert level screen 266 may include increase buttons 268 and decrease buttons 270 that may be selected by the medical personnel to adjust the high and low ICP level thresholds. By selecting the increase buttons 268, the respective high and low ICP level threshold may increase by a predetermined increment (e.g., 1 mmHg, 5 mmHg, 10 mmHg, etc.) with each selection of the button 268. By selecting the decrease buttons 270, the respective high and low ICP level threshold may decrease by a predetermined increment (e.g., 1 mmHg, 5 mmHg, 10 mmHg, etc.) with each selection of the button 270. After the medical personnel has set the high and low ICP level thresholds at the desired setting, a return button 272 can be selected on the ICP alert level screen 266 to return to the home screen of the GUI 18.

Figure 33:
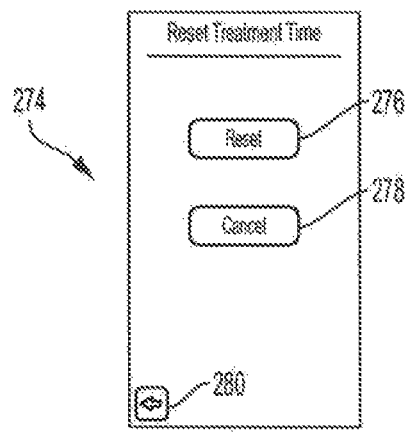
FIG. 33 is an illustration of a reset treatment time screen for the GUI of the present disclosure.

With reference to FIG. 33, a reset treatment time screen 274 is illustrated and described. The reset treatment time screen 274 may be accessed by selecting the treatment time indicator 92 on the home screen of the GUI 18. The reset treatment time screen 274 may include a reset button 276 and a cancel button 278. By selecting the reset button 276, the medical personnel can reset the treatment time indicator 92 to zero to restart the treatment time counter. By selecting the cancel button 278, the reset treatment time screen 274 returns to the home screen of the GUI 18. A return button 280 may also be provided on the reset treatment time screen 274 to return to the home screen of the GUI 18.

Figure 34:
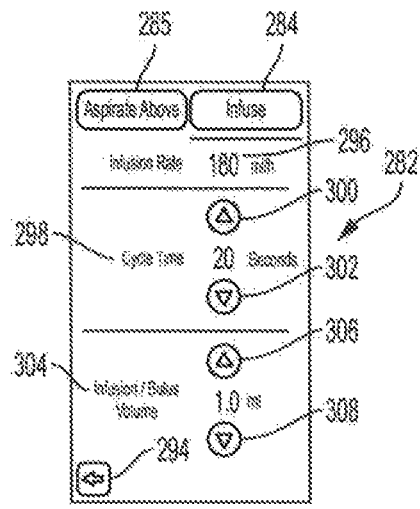
FIG. 34 is an illustration of an infusion rate and bolus screen for the GUI of the present disclosure.
Figure 35:
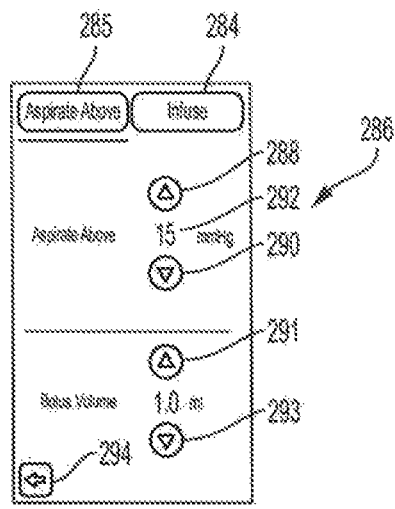
FIG. 35 is an illustration of a preset mode screen for the GUI of the present disclosure.
Figure 36:
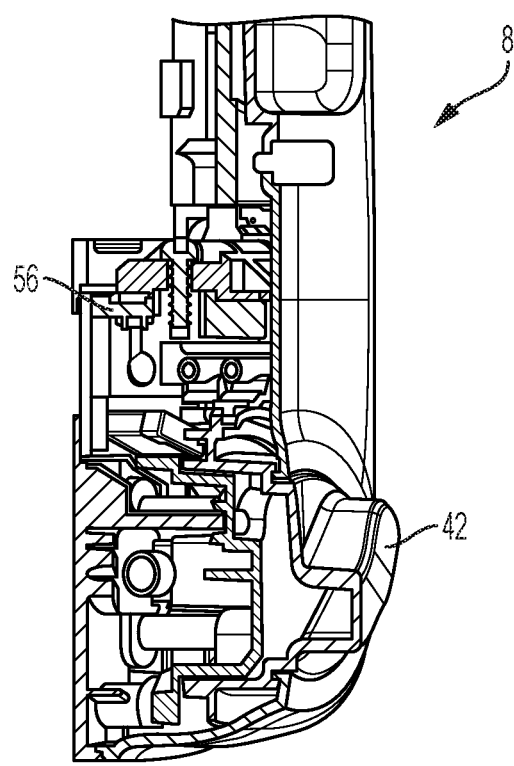
FIG. 36 is a cross-sectional view of the tube set attachment of FIG. 5A.

With reference to FIG. 34, an infusion rate and bolus screen 282 is illustrated and described. The infusion rate and bolus screen 28 may be accessed by selecting the patient fluid flow indicator 90 or the flow rate indicator 102 on the home screen of the GUI 18. The infusion rate and bolus screen 282 may include an infusion button 284 that may be selectable by the medical personnel to direct the GUI 18 to the infusion rate and bolus screen 282. The infusion rate and bolus screen 282 may also include an aspiration screen button 285 to direct the GUI 18 to an aspiration screen 286, as shown in FIG. 35. The aspiration screen 286 may include an increase button 288 and a decrease button 290 to change an aspiration level threshold 292. The aspiration level threshold 292 corresponds to the ICP level threshold of the patient that must be exceeded for the control unit 4 to begin an aspiration process to relieve ICP levels in the patient. The medical personnel may adjust the aspiration level threshold 292 by pressing the increase and decrease buttons 288, 292. The aspiration screen 286 may also include increase and decrease buttons 291, 293 to adjust the bolus volume of the control unit 4. The medical personnel may adjust the bolus volume by pressing the increase and decrease buttons 291, 293. The aspiration screen 286 may also include a return button 294 to return to the home screen of the GUI 18.

The infusion rate and bolus screen 282 may also include an infusion rate indicator 296 to display the current infusion rate of the control unit 4. The infusion rate and bolus screen 282 may also include a cycle time indicator 298 that indicates the current cycle time setting for the medical personnel. The cycle time corresponds to the infusion and aspiration cycle of the system 2. The cycle time indicator 298 may include an increase button 300 and a decrease button 302 to permit the medical personnel to adjust the cycle time according to the needs of the patient. The cylinder time may be increased or decreased by a certain time allotment (e.g., one second, ten seconds, fifteen seconds, thirty seconds, etc.) with each press of the increase or decrease button 300, 302. The infusion rate and bolus screen 282 may also include an infusion/bolus volume indicator 304. The infusion/bolus volume indicator 304 presents the current volume setting for the bolus volume that is directed through the system 2 when the medical personnel activates the bolus procedure. The bolus volume may be adjusted by the medical personnel by selecting an increase button 306 or decrease button 308. The bolus volume may be increased or decreased by a certain volume allotment (e.g., one mL, five mL, ten mL, etc.) with each press of the increase or decrease button 306, 308.

The preparation, installation, and operation of the system 2 is now described in greater detail. The control unit 4 is first placed in a vertical position on the IV pole 6 using the tightening knob 28 and IV pole clamp 24. A zero line 31 of the control unit 4 can be positioned at the same horizontal position with a patient's external auditory meatus. The control unit 4 can then be activated by pressing the power button 74. In one aspect, the control unit 4 may prompt a medical personnel to set a date and time in the control unit 4. The fluid source 10 may also be positioned on the IV pole 6.

After the control unit 4 has been attached to the IV pole 6 and the control unit 4 has been activated, the tube set attachment 8 may be connected to the control unit 4. The cassette 40 of the tube set attachment 8 is inserted into the connection port 16 of the control unit 4 to connect the tube set attachment 8 thereto. The tubing of the fluid source 10 is then connected to the tube set 36 of the tube set attachment 8. In one aspect, a male luer connector of the tube set of the fluid source 10 is connected to a female luer connector of the tube set 36 of the tube set attachment 8. In one aspect, the drainage receptacle 12 may be pre-connected to the tube set 36 of the tube set attachment 8.

Before use of the system 2, the tube set 36 of the tube set attachment 8 may be primed. With the tube set 36 connected to the fluid source 10 and the drainage receptacle 12, the calibration knob 42 on the cassette 40 is moved to an operating position. A medical personnel can then initiate a priming sequence using the control unit 4 to direct fluid from the fluid source 10 through the tube set attachment 8 and into the drainage receptacle 12. This priming sequence is continued until the complete tube set 36 is filled with the fluid. In another aspect, the tube set 36 of the tube set attachment 8 may be primed manually with a syringe. After the priming sequence has been completed, a portion of the tube set 36 is inserted into the air sensor 30 on the control unit 4 to monitor whether the fluid source 10 has been depleted. The drainage receptacle 12 can then be hung on the drainage receptacle hanger 32 on the control unit 4. The vertical position of the drainage receptacle 12 can be adjusted by adjusting the length of the graduated measuring band 34. By lowering the drainage receptacle 12, an aspiration flow is expected to increase for the system 2. By elevating the drainage receptacle 12, the aspiration flow of the system is expected to decrease. The aspiration flow of the system 2 is a gravity flow.

After the drainage receptacle 12 has been properly positioned, the system 2 may be calibrated. The calibration knob 42 on the control unit 4 may be turned to a calibration-mode. In the calibration-mode, the pressure sensors 56, 60 are connected to atmospheric pressure and a pressure signal is set to a zero value. With the calibration knob set to the calibration-mode, the medical personnel waits until the ICP value is zero. At this point, the pressure sensors are now calibrated. The calibration knob 42 may then be turned to the operational-mode to place the tube set attachment 8 in a position for treatment.

After the tube set attachment 8 has been calibrated, the catheter 44 is inserted into the patient's intracranial cavity using any method known in the art. The catheter 44 is then connected to the tube set 36 of the tube set attachment 8. The control unit 4 should then be set to initiate a desired treatment process. Initially, the medical personnel should set the desired upper and lower pressure alarms. Due to the patient's condition and desired treatment, the medical personnel can set the high ICP pressure setting and the low ICP pressure setting that should be monitored by the control unit 4. The medical personnel should also set the desired flow rate using the control unit 4. After this information has been set, the treatment process may be initiated by pressing the start/stop button 76. The treatment process that is initiated by the control unit 4 will be described in greater detail below. The medical personnel can periodically start and stop the treatment process using the start/stop button 76. In one aspect, the treating process may need to be stopped so the patient can be disconnected from the system 2 for an MRI or CT scan.

At any time during the treatment process, the medical personnel can change the flow rate setting by pressing the flow rate indicator 102, which will prompt the GUI 18 to allow the medical personnel to raise or lower the flow rate of the system 2. In a pre-set mode of the treatment process, no infusions are made to the patient and only aspiration occurs when the measured ICP is greater than the high ICP setting. A high flow rate setting may be used when draining a hemorrhage. A lower flow rate setting may be used for ICP monitoring and draining of clearer fluid from the intracranial cavity.

The medical personnel also has the option to flush the catheter 44 and tube set 36 before or after the treatment process. By pressing the bolus button 78 on the GUI 18, a bolus injection from the fluid source 10 is directed through the catheter 44 and the tube set 36. When flushing the system 2, aspiration does not take place. The bolus feature may be used according to the discretion of the treating medical personnel.

The treatment process performed by the system 2 includes the use of a drug or drug combination for treating a human or animal body by surgery or therapy, in which a catheter 44 of the present disclosure is used. In one aspect, the drug or drug combination is administered to a patient by the catheter 44 or system 2 of the present disclosure. In one aspect, a drug combination includes at least two drugs. In another aspect, a drug or drug combination for use in a diagnostic method practiced on the human or animal body is disclosed, which utilizes the catheter 44 or system 2 of the present disclosure. In one aspect, a fluid administered by the system 2 is a physiological solution. That is, physiological solutions (which are generally not limited, and are well-known to the skilled person), such as NaCl 0.9% or ringer's lactate solution, may be administered (and optionally aspirated) by a catheter 44 of the disclosure. In other aspects, the fluid is a nutrient solution.

In general herein, "at least one drug" may refer to one drug. In other aspects herein, "at least one drug" may refer to "at least two drugs." In other aspects herein, the terms "at least one drug" and "at least two drugs" may refer to two, three, four, five, or six drugs, preferably two three or four drugs, preferably three drugs, preferably two drugs. In certain aspects, the drugs used herein, such as the "at least two drugs," are incompatible. Incompatible drugs are not particularly limited and are readily known to the skilled person, e.g. from standard handbooks on injectable drugs. In certain embodiments, incompatible drugs are not compatible for y-site injection and/or for injection in a single syringe. In exemplary aspects herein, the "at least two drugs" are administered simultaneously. In other aspects herein, the "at least two drugs" are administered sequentially. In certain aspects herein, the at least one drug or at least two drugs may be a drug combination of any of the drugs described herein.

The system 2 manages the flow of infused and aspirated fluids through the catheter 44. As mentioned above, the control unit 4 is a software-based management system using certain algorithms to enable pump and sensor control and appropriate delivery of the therapy to the patient, body cavity or tissue. Infusion and aspiration flow management can be performed by a valve function capable of alternately restricting and permitting fluid flow, and therefore, fluid pressure to the tubing, catheter, distal lumen, distal ports, targeted tissues, and body cavity. In the present disclosure, a valve can be used to manage aspirated fluid, while infused fluid is managed by pump function. The valve function is steered by the control unit 4 according to the algorithm and desired therapy, in which the protocol performed by the controller, pump, and valve includes a programmed, alternating series of infusion, aspiration and pauses, in any therapy-appropriate combination thereof. During any of these flow phases, the control unit 4 operates the pump 66 and valve to determine flow rate, fluid pressures within the system, and body cavity pressures. The valve is constructed in a manner to both act on the tube set 32 as a pinch valve 64 and to allow insertion, threading or feeding of the tube set 32 into the control unit 4 and through the valve. The valve itself is constructed to function as a pinch valve 64 through axial displacement against the tubing, for example as a linear solenoid. The valve may also be constructed as a cantilever mechanism, roller mechanism, wedge, or tubing deflection mechanism.

Figure 12:
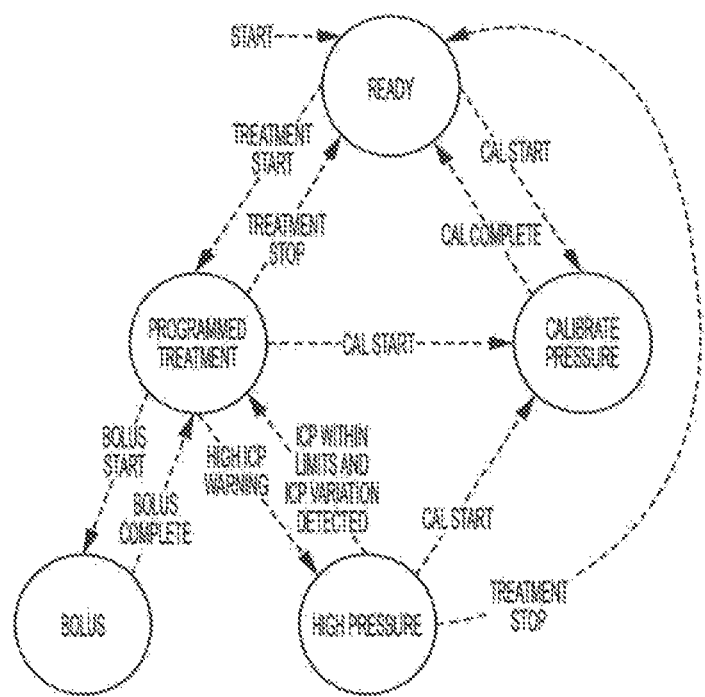
FIG. 12 is a flowchart illustrating different treatment states for the fluid exchange system of FIG. 1.

The CPU of the control unit 4 controls the treatment process of the system 2 and is, in one aspect, organized as a finite state machine. The CPU can operate in various states with different events determining when and how the transitions between states occur. With reference to FIG. 12, exemplary states and the events that cause transitions between the states are shown and described. The CPU may be held in a ready state, in which the system 2 remains idle. The system 2 can require certain conditions to be met before entering a programmed treatment state and/or calibration state. For example, before entering the programmed treatment state, the system 2 can first ensure that the cassette 40 is connected to the control unit 4, the pressure sensors 56, 60 are calibrated, the air sensor 30 indicates that there is fluid in the tube set 36, any periodic monitoring tests are cleared, and/or the start/stop button 76 is pressed by the medical personnel to initiate the programmed treatment process with the system 2.

Another state is the calibration state, which can be reached from the ready state or the treatment state. The calibration state is used to ensure the system 2 and the components thereof are properly calibrated. The control unit 4 may enter the calibration state by, for example, moving the calibration knob 42 on the control unit 4 to the calibration position. Upon entering the calibration state, a zero offset value for each pressure sensor 56, 60 can be determined. To determine the zero offset value, a delay for a minimum of 500 ms to allow settling of any raw signal is initiated. An average of raw pressure reading samples are then taken over a brief period, such as a period of one second or less. The averaged value is then stored as the zero offset value for each pressure sensor 56, 60.

After calibration has been completed, the control unit 4 may be moved to the programmed treatment state. However, in some embodiments, such as where the system was recently calibrated, it is not necessary to first complete the calibration process before entering the programmed treatment state. The programmed treatment state can be used to infuse and/or aspirate a fluid to and from a patient. While in the treatment state, the control unit 4 can sequence through different treatment parameters selected by the user to move between different infusion and aspiration states. During the infusion states, the control unit 4 is configured to supply and direct fluid from the fluid source 10, through the tube set 36, and to the patient, such as to the patient's intracranial cavity. During the aspiration states, the control unit 4 is configured to drain fluid from, for example, the intracranial cavity through the tube set 36 and into the drainage receptacle 12. The pump 66 of the control unit 4 can create positive pressure in the tube set 36 or a particular lumen thereof to pump fluid to the patient during the infusion states, and can create negative pressure in the tube set 36 or a particular lumen thereof to drain fluid from the patient during the aspiration states. Exemplary infusion and aspiration programs include those discussed in U.S. Pat. No. 8,398,581 and United States Patent Application Publication No. 2015/0224284, the disclosures of which are incorporated herein by reference.

The control unit 4 may be preprogrammed to switch between the infusion and aspiration states based on desired results from the medical personnel. In another aspect, the control unit 4 may switch between the infusion and aspiration states based on pressure readings recorded by the pressure sensors 56, 60. In particular, the pressure sensors 56, 60 may send ICP readings to the control unit 4, which monitors the ICP levels of the patient. In the event the ICP readings are in the desired ranges, the control unit 4 continues to run the preprogrammed treatment process. In the event the ICP readings exceed the high ICP level setting, the control unit 4 may be configured to initiate the aspiration state to drain fluid from the patient's intracranial cavity to reduce the ICP. After a sufficient volume of fluid has been drained from the intracranial cavity and the ICP level has been reduced between the ICP high level setting, the control unit 4 may be configured to resume the preprogrammed treatment process. In another aspect, in the event the ICP readings fall below the low ICP level setting, the control unit 4 may be configured to initiate the infusion state to direct additional fluid to the patient's intracranial cavity. After the fluid has been directed to the intracranial cavity and the ICP readings increase above the low ICP level setting, the control unit 4 may be configured to resume the preprogrammed treatment process. In another aspect, a treatment stop event for the control unit 4 will return the system 2 to the ready state. The treatment stop event may be initiated by the medical personnel pressing the start/stop button 76. It is also contemplated that the control unit 4 may be automatically returned to the ready state in the event an emergency situations occurs with the control unit 4 and/or patient.

In one aspect, the control unit 4 may move between the infusion and aspiration states using several different techniques. In one aspect, the pressure sensors 56, 60 may measure a first pressure value in the intracranial cavity and send this measurement to the control unit 4. An infusion of fluid into the intracranial cavity may then be initiated by the control unit 4. After the infusion state, the pressure sensors 56, 60 may measure a second pressure value in the intracranial cavity and send this measurement to the control unit 4. The CPU of the control unit 4 may then compute or determine a difference between the first and second pressure readings from the pressure sensors 56, 60. In the event the difference between the first and second pressures exceeds a high threshold level, the control unit 4 may issue a high pressure signal output. The control unit 4 may then initiate an aspiration state to reduce the ICP. In the event the difference between the first and second pressures is below a low threshold level, the control unit 4 may issue a low pressure signal output. The control unit 4 may then initiate an infusion state to increase the ICP.

The system 2 may use measurements of "compliance" and "elastance" to regulate the treatment process. In general, the adult vertebrate cranium is a rigid structure. Major intracranial contents are the brain, blood, and cerebrospinal fluid (CSF). Since the intracranial volume is constant, when an intracranial mass is introduced compensation must occur through a reciprocal decrease in the volume of venous blood and CSF. This is known as the Monro-Kellie-Burrows doctrine. To maintain pressure within the physiologic range, the venous system of the patient collapses easily, squeezing venous blood out through the jugular veins or through the emissary and scalp veins. CSF, likewise, can be displaced through the foramen magnum into the spinal subarachnoid space. When these compensatory mechanisms have been exhausted, minute changes in volume produce precipitous increases in pressure (e.g. in the range of 1-5 ml depending upon the associated timing).

Compliance ($dV/dP$) is the change in volume observed for a given change in pressure. This represents the accommodative potential of the intracranial space. Compliance is high when a cranial cavity will permit the accommodation of a large mass with very little change in pressure. In clinical practice, however, what is measured usually is elastance ($dP/dV$), the inverse of compliance, which is the change in pressure observed for a given change in volume. It represents the resistance to outward expansion of an intracranial mass. Elastance can be measured at the bedside, for example, by injecting 1 ml of sterile saline through the ventricular catheter and observing the change in pressure. An increase of less than 2 mm Hg implies low elastance and high compliance. The high risk of infection associated with this maneuver, however, precludes regular performance as a pressure measurement method.

In one aspect, the control unit 4 can measure compliance, for example, after each infusion of 1 ml (or less volume) without infection risk by analyzing the pressure curve created and thus provide valuable information on the actual and anticipated ICP values of the patient. The medical personnel will be alerted when there is a trend of compliance values going up or down, in order to act earlier and modify treatment accordingly for the patient's benefit. The same concept may be applied in monitoring the local pressure and compliance of any body organ and tissue during treatment, for example, to protect the organ from malfunction or rupture.

Measurement of compliance and elastance according to the present disclosure may be accomplished in any of a variety of suitable manners. For example, compliance measurement of the present disclosure may be described as an ex vivo method for determining the cerebral compliance in the intracranial cavity of a patient.

One example of the compliance measurement by the control unit 4 is described below. In one aspect, by measuring the first pressure in the intracranial cavity, the control unit 4 can provide a first temporal progression curve of pressure corresponding to the first measured pressure value. By measuring a second pressure in the intracranial cavity, the control unit 4 can provide a second temporal progression curve of pressure corresponding to the second measured pressure value. In one aspect, a first derivative may be determined by the control unit 4 from the first measured pressure value. A second derivative function may be determined by the control unit 4 from the second measured pressure value. The control unit 4 may then determine a first maximum slope value of the first derivative function and a second maximum slope of the second derivative function. The control unit 4 may then determine a difference between the first maximum slope value and the second maximum slope value. Based on the difference between the first maximum slope value and the second maximum slope value, the control unit 4 may determine a cerebral compliance value. The measured cerebral compliance value may be compared to a previously-measured cerebral compliance value. In the event the cerebral compliance value exceeds a threshold value, a signal output may be issued by the control unit 4 to notify the medical personnel. The control unit 4 may then determine if a liquid infusion can be administered immediately after a predetermined time interval has elapsed. The predetermined time interval may be a time interval that allows the cerebral compliance to decrease under the threshold value.

With reference again to FIG. 12, during the programmed treatment state, the control unit 4 may initiate a bolus state. The bolus state may be initiated when the medical personnel presses the bolus button 78 on the GUI 18 while in the programmed treatment state. In the bolus state, the control unit 4 is configured to send a bolus infusion through the tube set 36.

During the programmed treatment state, the control unit 4 may issue a high ICP warning. This high ICP warning will initiate the high pressure state for the control unit 4. This state of the control unit 4 can wait to verify the natural ICP variation from the patient's heart rate is present and that ICP is within the user set limits. After these conditions have been met, the control unit 4 will transition back to the programmed treatment state and the treatment sequence will be reinitiated. While aspirating a brain with high pressure, for example, there is a risk of ventricular collapse, which means that the cavity where the catheter 44 is sitting is drained of most or all fluid. The walls of the ventricle may then act as a check valve, letting fluid in but not out and will stop the pressure sensors 56, 60 from measuring the correct ICP. The system 2 could then end up in a situation where fluid is infused into a brain with high ICP. If a variation of the ICP that naturally occurs in the patient's intracranial cavity resumes, then the system will understand that the fluid is positioned around the catheter 44 and is measuring the correct ICP.

During the programmed treatment state or any other state, the control unit 4 may automatically enter the failure state if a non-recoverable device failure is detected. In one aspect, non-recoverable device failures may include internal software errors, monitored voltage being out of tolerance, the safety module 58 is not responding to commands, and the safety module 58 has detected a non-recoverable error. When the failure state is entered, the pinch valve 64 of the control unit 4 is closed, the pump 66 is stopped, and a message will be displayed on the GUI 18 instructing the medical personnel that the control unit 4 must be restarted.

The control unit 4 may also be capable of managing pressure in the system 2 by steering pump motor function in order to apply or reduce pressure in the tube set 36, catheter 44, or body cavity. The pump 66 can be stepped forward to apply incremental pressure and, similarly, stepped incrementally back to reduce pressure. Control unit interpretation of pressure differentials and pressure wave forms in the system 2 enables management of pump function to deliver and alter the intended therapy, provide feedback to the user, or trigger alarms. The same data also provides feedback on system function, including restriction or blockage in the catheter 44 or tube set 36. Data is acquired from a combination of sensors 56, 60 in the catheter 44, tube set 36, fluid container(s), and combined motor and sensor function. Blockage in the catheter 44 can be detected, for example, by applying a sudden burst of pressure from the pump 66 to initiate a pressure wave. Sensors 56, 60 in the catheter lumen and/or catheter tip can be used to detect the fluid reflex as a result of the induced pressure wave, thereby detecting the existence of restricted or blocked fluid flow through the lumen. Similarly, pump motor operating parameters, including current, power consumption and motor position, are also monitored by the control unit 4 to manage system function.

Figure 13:
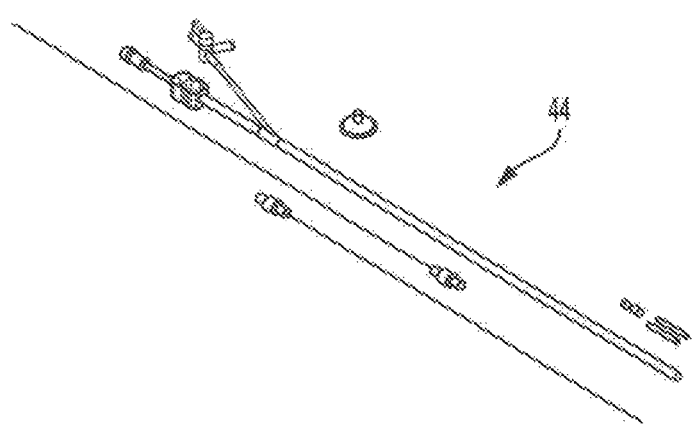
FIG. 13 is a perspective view of a catheter according to one aspect of the present disclosure.
Figure 14:
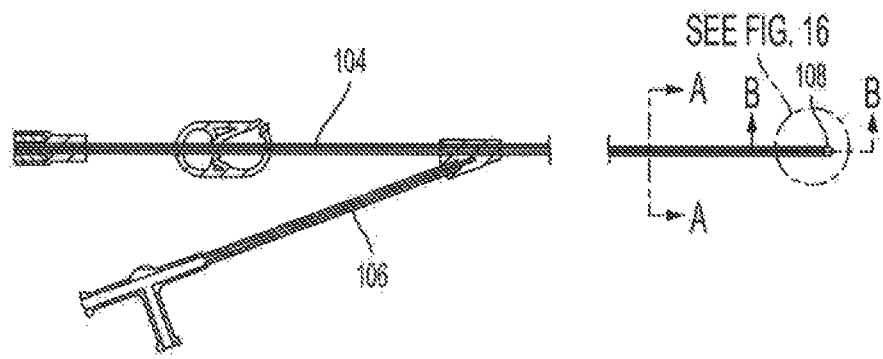
FIG. 14 is a cross-sectional view of the catheter of FIG. 13 taken along line A-A.

With reference to FIGS. 13 and 14, the catheter 44 used in the system 2 is shown and described. The catheter 44 may include a variety of features that focus on achieving the desired infusion and aspiration functions of the system 2. Several of these features are shown and described in U.S. Patent Application Publication No. 2015/0224284, the disclosure of which is hereby incorporated in its entirety by reference. For purposes of this disclosure, the tip of a catheter 44 that is inserted in biological material, e.g. the patient's body, is called the distal tip or distal end of the catheter 44 and the tip that stays outside of the biological material is called the proximal tip or proximal end of the catheter 44.

Figure 15:
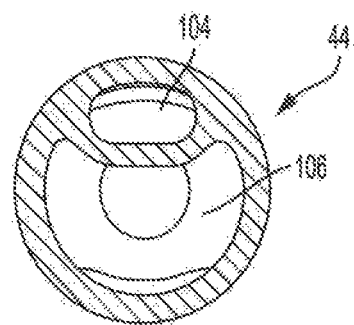
FIG. 15 is another cross-sectional view of the catheter of FIG. 13 taken along line B-B.

As shown in FIGS. 14 and 15, the catheter 44 may be a dual lumen catheter. The catheter 44 may include an infusion lumen 104 and an aspiration lumen 106 that are each created by one or more lumen walls that extend generally from a proximal end to a distal tip 108 of the catheter 44. It is to be understood that the specific lumina may be switched, i.e., the infusion lumen 104 and the aspiration lumen 106. In one aspect, the infusion lumen 104 may act as the outer catheter body. In one aspect, the infusion and aspiration lumina 104, 106 branch off from one another at an intermediate position on the catheter 44. In one aspect, the aspiration lumen 106 may be defined in the infusion lumen 104 along the length of the catheter 44 in which the infusion and aspiration lumina 104, 106 converge. In one aspect, infusion fluid from the fluid source 10 is directed through the infusion lumen 104. In one aspect, fluid aspirated from the intracranial cavity to the drainage receptacle 12 is directed through the aspiration lumen 106. However, the infusion lumen 104 and aspiration lumen 106 are each structurally configured to allow for infusion or aspiration to occur therein, depending on the particular direction of flow enabled by the device attached at a proximal end thereof.

Figure 16:
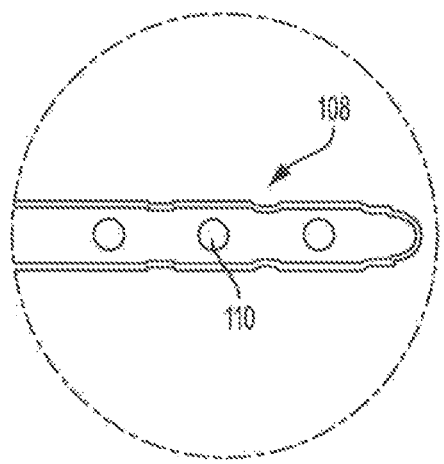
FIG. 16 is a cross-sectional view of a distal tip of the catheter of FIG. 13 taken along line B-B.

As shown in FIG. 16, the distal tip 108 of the catheter 44 may include a plurality of apertures 110 and/or may have a porosity, generally described as openings or ports. These apertures 110 are designed to achieve the desired performance for infusion of therapeutic fluids and evacuation of targeted tissues and fluids and solids of various character, as may occur in relation to treatment of the disease or the delivered therapy. The apertures 10 play a multifaceted role to allow optimal rates of both fluid infusion and fluid aspiration, as well as maintaining free, unhindered flow through the system 2. Specific design elements that affect the performance of the apertures 110 in the distal tip 108 are, for example, the size of the apertures 110, the position of the apertures 110 on the catheter length or tip 108, the position of the apertures 110 relative to the target or surrounding tissue when in use, the position of the apertures 110 relative to the aspiration lumen 106 of the catheter 44, the direction of fluid flow to and from the aspiration lumen 106 relative to the apertures 110, and the cross-sectional flow area of the apertures 110 relative to the flow area of the aspiration lumen 106.

These features, among others, affect the ability of the catheter 44 to perform its infusion and aspiration function as specified and desired.

The present disclosure may also include a host of additional catheter features. For example, the catheter 44 may be configured to achieve a multifunctional self-regulating endoscopic system, including (by way of example only) one or several of the following components: an optical fiber for observation and/or video recording; an additional outer lumen for guiding a biopsy stylet, a microforceps, or the like for biopsy or local tissue manipulation; one or several electrodes for monopolar or bipolar coagulation; a microdialysis catheter for biochemical and pharmacokinetic monitoring; one or more sensors within or associated with the catheter 44 (e.g. a pressure sensor, a temperature sensor, a pH value sensor, a sensor for a specific molecule or chemical compound, or the like); a local irradiation probe; and an ultrasound probe for imaging and energy delivery, which are both useful for monitoring and lysing a blood clot, respectively. For example, with an endoscopic system as cited above, drugs can be infused while, for example, an ultrasound treatment and/or a microdialysis process can be carried out simultaneously, followed, e.g., by pressure and temperature measurement and drainage. Further, instead of merely evacuating substances, it is also possible to gather tissue or fluid samples while administering drugs to the body or the target tissue. As a particular example of such a system for the treatment of, for example, a solid malignant tumor, such an endoscopic system may be introduced into the inside of a pancreatic tumor under radiological inspection.

The catheter 44 of the present disclosure may include one or more of the following features: a large lumen including a stylet or the like, for example, for the introduction of the catheter 44 into a pancreatic tumor under radiological inspection and/or its own imaging ability through a small incision of the abdominal wall of the patient; an optical fiber, usable, for example, for direct inspection of the introduction of the catheter 44 into the tumor and/or video-recording of the procedure in case radiological inspection is not desirable and/or sufficient for patients' safety; an ultrasound probe usable, for example, for direct inspection of the introduction of the catheter 44 into the tumor and monitoring of its dimensions throughout the whole therapy (ultrasound energy may also enhance the drug regimen's potency); an infusion lumen, for example, for infusion of ringer's lactate solution, which infusion lumen can be provided inside an aspiration lumen also containing any other feature such as the above mentioned optical fiber, the solution being usable, for example, for washing the optical fiber's tip and clearing the surgeon's view; biopsy stylet or the like, usable, for example, for biopsies of a tumor after introduction i.e. after stylet's withdrawal; microsurgical instruments, for example, for local tissue manipulations apart from biopsy (like microforceps for tissue dissection, usable through the central lumen of the catheter 44); electrodes provided, for example, around the catheter 44, which electrodes can be usable, for example, for bipolar coagulation of a bleeding during introduction of the catheter 44, for example, during surgical manipulations and/or during withdrawal of it out of the patient's body, or usable for changing the physiological environment of the treatment site; a combination of three or more infusion lumina to be introduced into the large lumen, for example, after withdrawal of the biopsy stylet, usable, for example, for simultaneous administration of a cytotoxic chemotherapeutic drugs solution, an analgesic solution and an isotonic physiological solution for local drug concentration, temperature, pressure and/or pain control; a microdialysis catheter usable, for example, for local biochemical and/or pharmacokinetic monitoring; sensors at the tip of the catheter connected appropriately, usable, for example, for the monitoring of local physicochemical parameters (like temperature, pHvalue, ICP, etc.); and/or a local irradiation probe, for example consisting at least in part of Iridium, usable, for example, through a central lumen for local irradiation of the tumor after chemotherapy and before withdrawal of the catheter 44 out of the body. The mentioned drug and/or physiological fluid infusions can be administered for a period of several days, and can be adjusted according to biochemical and/or physicochemical local parameters, in order to enhance the drug's potential. Further, additional lumen can be introduced in case, for example, antidote administration for reversing drug toxicity and/or parallel administration of drugs designed to interact for maximum therapeutic potential when administered simultaneously inside the pathology are needed. Such information, potentially combined with the biochemical information provided by the microdialysis catheter, can assist a doctor to optimize and individualize, for example, a chemotherapy treatment to be administered, according to a reaction of malignant tissue to be treated. From time to time, new biopsy samples of tissue can be extracted and analyzed, if needed. For this reason, the combination of three infusion lumen can be temporarily taken out in order to perform, for example, biopsy-sampling with appropriate stylets, microforceps or the like.

Several embodiments of multi-lumen catheters can be considered to achieve the best performance of infusion, aspiration, general flow, and/or unblocking of the catheter 44. The following individual embodiment descriptions may include features that can advantageously be included in other listed embodiments and are not exclusive to one embodiment, but can be interchanged by a person skilled in the art, where appropriate.

In one aspect, the apertures 110 included in the walls of the various catheter lumina 104, 106 are positioned so that infused fluids can be employed to clear obstructions from the apertures 110 in order to maintain effective removal of fluids and small particulates from a body cavity or tissue. In this design, the apertures alignment is intended to direct flow of infused fluids radially toward the apertures 110 and, thereby, improve unblocking of the apertures 110. Apertures 110 are also provided in the wall of the infusion lumen 104 such that the apertures 110 are substantially in alignment, both axially and radially, with the apertures 110 provided in the aspiration lumen 106. Aligned aperture 110 pairs in the infusion lumen 104 and the aspiration lumen 106 may be distributed axially so as to occur across different cross-sectional planes along the length of the catheter 44, for example in a staggered, repeated or random pattern. Infusion may occur as a steady stream or shorter injections of fluid directed toward the aligned apertures 110. The catheter 44 is formed as a multi-lumen extrusion such that the infusion lumen 104 may be formed as a co-extrusion of the wall of the outer catheter body, formed as a substantially separate lumen attached to the inner surface of the outer catheter body, is a separate, telescopically arranged lumen, or any combination thereof.

Additional lumina can also be used for the aspiration and collection of tissues and fluids from a body cavity, separately form the aspiration function of the main lumen. This can include collection of pathological fluids and tissues, septic fluid collection, fluid or blood sampling, drainage, sampling of tissues of fluids for measurement or therapeutic monitoring and/or even collection of general tissue samples. Additional lumina may be positioned radially at any point on the circumference of the catheter's 44 outer diameter. The additional lumina may also be constructed as separate lumina within the outer catheter body or constructed as a bore in a thicker wall of the infusion lumen 104 or outer catheter body. The infusion lumen 104 can include apertures to both the inner, aspiration lumen, on the external diameter of the catheter body; or between infusion lumen. Several embodiments can be considered wherein individual embodiment descriptions may include features that can be included in other listed embodiments and are not exclusive to one embodiment.

In a further aspect, the catheter 44 is formed as a multi-lumen extrusion with the aspiration lumen 106 substantially located as axial bores in the wall of the infusion lumen 104 or as co-extruded lumen immediately adjacent to the wall of the infusion lumen 104. The aspiration lumen 106 may intersect with the apertures 110. The apertures 110 are formed as slots, valves, holes, or any shape that provides drainage of media from a body cavity or tissue to the aspiration lumen 106 of the catheter 44. The infused fluid washes axially over the apertures 110 to remove particulate and/or buildup and help to keep the port clear and open for fluid flow. In another aspect, the catheter 44 is formed as a multi-lumen extrusion with the aspiration lumen 106 substantially located as axial bores in the wall of the infusion lumen 104 or as co-extruded lumen immediately adjacent to the wall of the infusion lumen 104. The aspiration lumen 106 may intersect with the apertures 110 and cross through the apertures 110 to a next infusion fluid exit port on the aspiration lumen 106 or external surface of the infusion lumen 104. In this manner, the apertures 110 and aspiration lumen 106 form a cross-formed intersection substantially within the catheter wall. The intersection between the aspiration lumen 106 and the aperture 110 are configured to create a venturi effect at their intersection by including a narrow section of the aspiration lumen 106 at the intersection. The venturi effect creates suction in the aperture 110, for example to assist in drawing aspirated media from either side of the catheter body into the aspiration lumen 106 and help to keep the apertures 110 open and unblocked.

In a further aspect, infusion lumina are included as bores in the wall of the outer catheter body 104 and ports are provided to allow infusion of fluids to either or both of the aspiration lumen 106 or to the tissues or body cavity surrounding the catheter. Infusion lumina may be designated for separate purposes, such as the infusion of separate fluids or agents. This design achieves multiple ports of exit for the infused fluid and may be employed to affect tissues and fluids both internal and external to the catheter 44.

Figure 17:
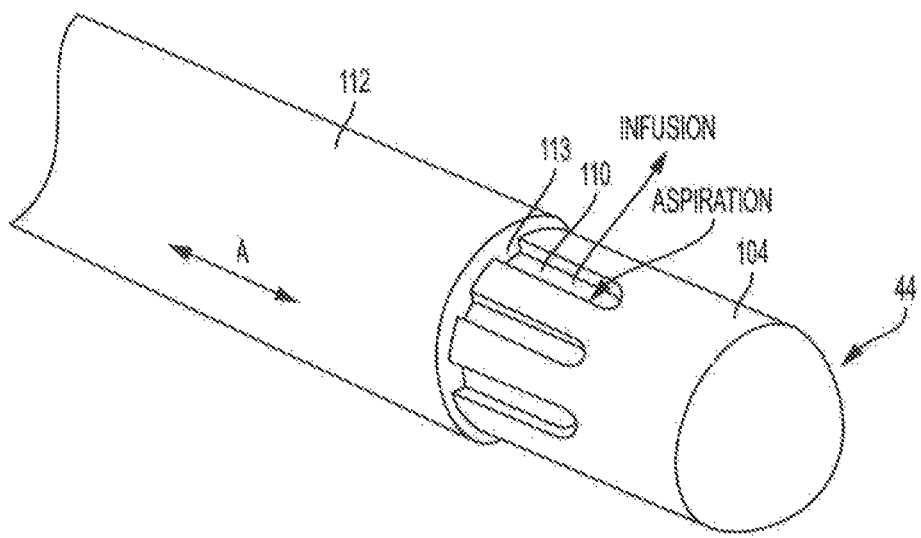
FIG. 17 is a perspective view of a distal tip of a catheter according to an aspect of the present disclosure.
Figure 18:
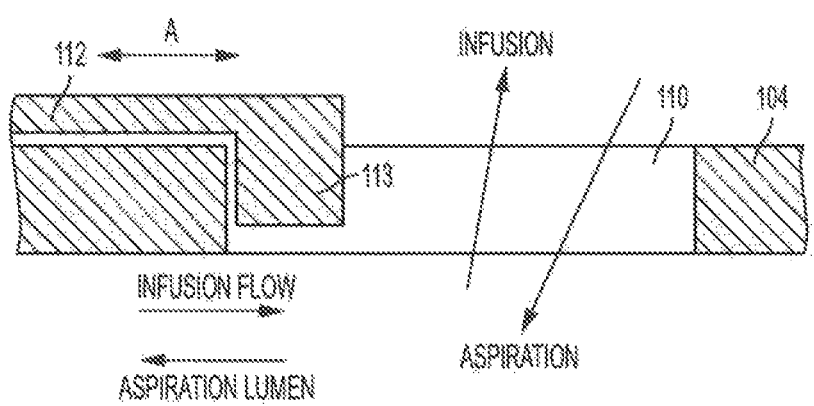
FIG. 18 is a cross-sectional view of the distal tip of the catheter of FIG. 17 taken along line B-B.

In another aspect shown in FIGS. 17 and 18, the catheter 44 may have a telescopic construction and may include a sleeve 112 over a hollow lumen or multi-lumen catheter 44. The sleeve 112 may slide over the outer surface of the catheter 44 so that the catheter 44 is substantially positioned within the sleeve 112. The sleeve 112 and the hollow lumen or multi-lumen catheter 44 are able to be displaced axially relative to each other so that the apertures 110 provided in the catheter 44 may be cleared of debris or obstructions. The sleeve 112 may also be used to restrict flow or close off the apertures 110, thereby also providing a valve function. The sleeve 112 may include at least one sleeve shoulder 113 that extends from an inner circumferential surface of the sleeve 112. The sleeve shoulders 113 are received in the apertures 110 of the catheter 44. The sleeve shoulders 113 are slidable within the apertures 110 to clear debris or obstructions that are caught in the apertures 110. The catheter 44 may include any interchangeable configuration of single or multiple lumina 104, 106 for infusion and aspiration of fluids and use of infused fluids to clear the apertures 110. The sleeve 112 may be moved in an axial direction A relative to the catheter 44. The sleeve 112 may move between a first position (shown in FIG. 17) in which the apertures 110 are closed, and a second position (shown in FIG. 18) in which the apertures 110 are open. With axial movement of the sleeve 112 relative to the catheter 44, the sleeve shoulders 113 may push or direct any debris or obstructions out of and away from the apertures 110.

Figure 19:
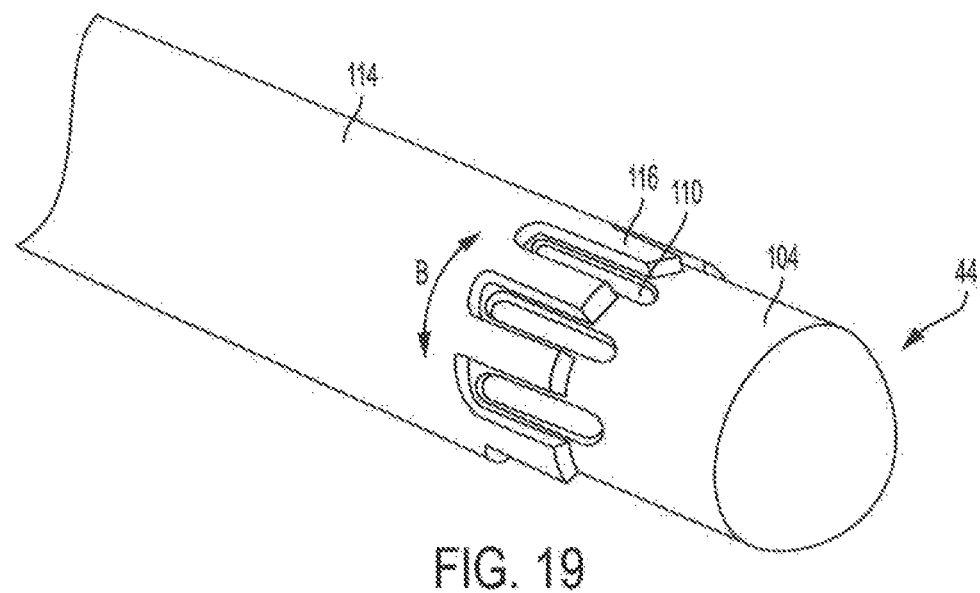
FIG. 19 is a perspective view of a distal tip of a catheter according to an aspect of the present disclosure.
Figure 20:
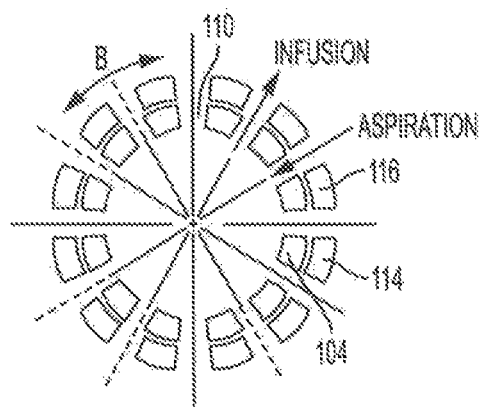
FIG. 20 is a cross-sectional view of the distal tip of the catheter of FIG. 19.

In another aspect shown in FIGS. 19 and 20, a sleeve 114 is provided over a hollow lumen or multi-lumen catheter 44. The sleeve 114 may slide over the outer surface of the catheter 44 so that the catheter 44 is substantially positioned within the sleeve 114. The sleeve and catheter combination is configured to clear the apertures 110 in a rotational manner. A plurality of sleeve elements 116 extending from the distal end of the sleeve 114 and positioned adjacent to the apertures 110 of the catheter 44 pass over the apertures 110 when the sleeve 114 and catheter 44 are rotationally displaced in relation to each other so that the apertures 110 may be cleared of debris or obstructions. The sleeve 114 may also be used to restrict flow or close off the apertures 110, thereby also providing a valve function. The catheter 44 may include any configuration of single or multiple lumina 104, 106 for infusion and aspiration of fluids and use of infused fluids to clear the apertures 110. The sleeve 114 may be rotated about a longitudinal axis of the catheter 44 in a direction B. The sleeve 114 may move from a first position in which the apertures 110 are closed, and a second position (shown in FIGS. 19 and 20) in which the apertures 110 are open. With rotational movement of the sleeve 114 relative to the catheter 44, the sleeve 114 may push or direct any debris or obstructions away from the apertures 110.

In the case of aspirated fluid moving from the apertures 110 to any of the aspiration lumina 106 interchangeably designated for aspiration of fluid, substances, tissue or any infused material from the body, the catheter's aspiration lumen 106 is designed to minimize resistance, hindrance or blockage within the catheter length during the evacuation of fluids and solids from the body cavity. Specific design elements included to achieve the desired unhindered flow can be catheter and tubing diameters or cross-sections that are sized according to the characteristics of the fluid they are intended to transport, position or offset of extruded cannula lumen relative to each other to avoid flow restrictions, cross-section dimension and length dimension ratios, and positional relationships between fluid management components to achieve desired flow characteristics. These components may include: catheter ports, lumen, tubing, cassettes, fluid management systems antimicrobial or particle or other filters, flow regulator devices, heating devices, and containers, i.e. all sections of the system where flow management can affect overall system performance.

The catheter 44 and tube set 36 are designed to avoid kinking and deformation related to flow obstruction Kinking may be avoided, for example, by selection of polymers used in the catheter 44 and tube set 36, structural elements such as reinforcing included in the catheter wall, extrusion design to resist wall and lumen collapse and separate structural components (wires or sheaths, for example) that may be inserted, removed or telescopically positioned to achieve a desired mechanical property. For example, kinking resistance can be designed into the extrusion cross-section by inclusion of a web between lumen or a structural web profile integrated into the lumen wall, wherein the web includes shapes, such as I-beams or other configurations of cross-sections that resist deflection, sharp angular deflection, torsion and any combination thereof in several directions. Such luminal cross sections may also vary or transition over the length of the catheter, tubing or lumen in order to achieve desired design and use characteristics such as atraumatic shapes, deflection, elasticity, push-ability, torsion resistance. Deflection and bending properties, including resistance to certain deformations, could also be achieved by functional components and materials embedded appropriately in the lumen wall. For example, functional components may include one or more optical fibers, bipolar electrodes, ultrasound probes, or conductive or signal transmitting leads, such as a wire for measuring pressure, temperature, tissue pH, and other properties.

The infusion and aspiration function of the catheter 44, tube set 36, and system 2 may also include one or more sensors as part of electronic control systems to achieve the desired function and flow. These may include sensors placed in the catheter tip, on an inner flow surface of the lumina, on the exterior of the lumen (in contact with the body cavity or surrounding tissue), integrated appropriately along the length of the catheter lumen, tubing, cassette, and/or in fluid containers to achieve the desired flow control, bio-physical feedback, and collect bio-chemical information from the patient. These sensors may be arranged to monitor pressure, flow, pump function, pressures within a body cavity, tissue properties, pH-values, among other parameters. For example, pressure sensors can be placed both internally to the catheter 44 and externally on the catheter 44 to measure differential pressure between the body cavity and the infused and/or aspirated fluid. Also, one or more MEMS-based sensors may be included to measure fluid velocity within the catheter 44 and determine if higher fluid velocity is needed to break up solids in the aspirated fluid and/or if lower velocities are appropriate for, e.g., aspiration of low viscosity fluids, or the like.

The catheter 44 may also include one or more lumen or guides enabling the passage and insertion of instruments to and beyond the distal tip of the catheter 44. Such instruments enable therapy and diagnosis directed at the tissues in the targeted body cavity adjacent to or in proximity of the catheter's distal end. For example, instruments delivered through the catheter 44 can include microforceps and similar endoluminal tools, vision tools like optical fibers, delivery tools for implants, such as radioactive seeds or probes, drug eluting implants, markers, adhesives, fasteners, ligation devices, hemostats, electrocautery instruments, microscalpels, dissection devices, balloons, and/or instruments for extraction of biopsy samples. Additional lumen can also be used for ultrasound equipment enabling imaging and visualization and/or energy transmission for lysing blood clots or tissue dissection. Additional lumina can also be used for tissue dissection through controlled jets of pressurized sterile water or physiological fluid.

Additional lumina also enable delivery of drugs or therapeutic agents and their antidotes for thrombolysis, coagulation, chemotherapy, infection management, hormone therapy, cell seeding, cell therapy, markers, and/or therapies applied directly to the targeted pathology and its surrounding tissue. Delivery of such agents may also be directed to the fluid within the infusion lumen 104 for purposes of mixing, dissolving or changing the character of infused or aspirated fluids. Generally, such drugs are not particularly limited to any category of pharmaceutical fluids. Drugs suitable for catheter administration are generally known to the skilled person, such as all eligible drugs for local infusion under the skin. At least one drug or several different drugs is/are selected from the group including antibiotics, anti-inflammatory drugs (e.g. corticosteroids, immune selective anti-inflammatory drugs, etc.), analgesics (e.g. non-steroidal anti-inflammatory drugs, opioids, etc.), chemotherapeutic drugs (e.g. alkylating agents, antimetabolites, anthracyclines, etc.), and hormones (e.g. insulin, HGH, etc.). The catheter 44 or system 2 of the present disclosure can also be used in the treatment of pain. Accordingly, in particular aspects, the (at least one) drug is selected from analgesics. Analgesics as used herein may include narcotics or the like.

In another embodiment, the catheter 44 or system 2 of the present disclosure is used in the treatment of cancer. Non-limiting examples for cancer include a pancreatic tumor, a liver tumor and a brain tumor, such as glioma or craniopharyngioma. Accordingly, in particular embodiments, the (at least one) drug is selected from chemotherapeutic drugs, such as from cytostatic and cytotoxic chemotherapy drugs. Non-limiting example for such drugs include fluorouracil, methotrexate, purine analogs, nitrosoureas, platinum compounds, alkylating agents, antitumor antibiotics, etc.

In particular aspects, the catheter 44 of the system 2 of the present disclosure is used for the removal of substances, such as undesired substances, from the body. Preferred examples of such substances are selected from the group including blood, coagulated blood, blood clot(s) (thrombus/thrombi), pus, toxic substance(s), superfluous drug(s), and/or pathological tissue(s). Other examples of such substances include tissue, such as tissue sample(s).

In one aspect, the catheter 44 or system 2 of the present disclosure is used in the treatment of cerebral vasospasm. In particular aspects, the catheter 44 of the present disclosure is used in the treatment of subarachnoid hemorrhage (SAH). The latter aspects may involve the clearing of subarachnoid blood and/or administered with the administration of at least one drug. Preferred non-limiting examples for such drugs are papaverine, urokinase, rTPA, etc. In one aspect, the catheter 44 or system 2 of the present disclosure is used as a self-regulating system, such as a self-regulating system not requiring the presence of a clinician, doctor and/or medical personnel, or a self-regulating system exceeding human capabilities as regards e.g. (rapid) treatment changes. In particular aspects, the catheter 44 of the present disclosure is used in an intensive care unit (ICU). In particular aspects, the catheter 44 or the system 2 of the present disclosure is used for monitoring a site within a patient's body, which monitoring may (by way of example only) include observation (direct and/or via closed circuit or other viewing technologies) and/or video-recording.

Flow control within the catheter 44 may be desired to provide a specified flow protocol, manage infusion and aspiration flow, or optimize the effect of infusion flow without loss of infused fluids to the aspiration tract, for example. In the present disclosure, flow control may be desired to optimize unblocking of the apertures 110 in the catheter body 104, more accurately mange infusion pressure to a body cavity or tissue by controlling a pressure relief pathway, or create a better agitation of media surrounding the catheter 44. To achieve this type of control, a valve 118 may also be integrated as part of the catheter 44 as a moving or deflecting element 120, a balloon 122, or using fluid resistance 124 to create a functioning obstacle or regulator of flow in the aspiration lumen or any lumen. The valve 118 can be activated by the infusion flow or separately by a mechanism, shape memory or shape induced element. The valve 118 may also be passively activated upon introduction of infusion pressure to an infusion lumen 104. That is, the valve 118 may be activated by controlled fluid infusion alone instead of by a separate electronic or mechanical valve device (for example, a door like cover of the infusion lumen's distal opening which is deflected by the infusion pressure as to cover fully the aspiration lumen 106 and comes back to its original position when infusion stops). The following embodiments can be considered to include a valve 118 in the catheter 44. The individual aspect descriptions may include features that can be included in other listed aspects and are not exclusive to one aspect.

In general, and with interest in safe operation, the control unit 4 or system 2 of the present disclosure may be designed to operate the valve 118 with a high-pressure default open position wherein the valve 118 is opened if intra-operative pressure (or body cavity pressure) is too high, based on sensor and pressure feedback data. Similarly, the control unit 4 or the system 2 conversely may operate the valve 118 with a low-pressure default closed position, in which the valve 118 is closed if intra-operative pressure (or body cavity pressure) is too low. Default valve positions, valve function to meter or restrict flow, and motor function appropriate to achieve (or in response to) specified flow and pressures may be dictated by the control unit, according to any set of sequences and appropriate algorithms, to perform the desired therapy protocol appropriate to the body cavity, tissue and disease or condition to be treated.

Figure 21:
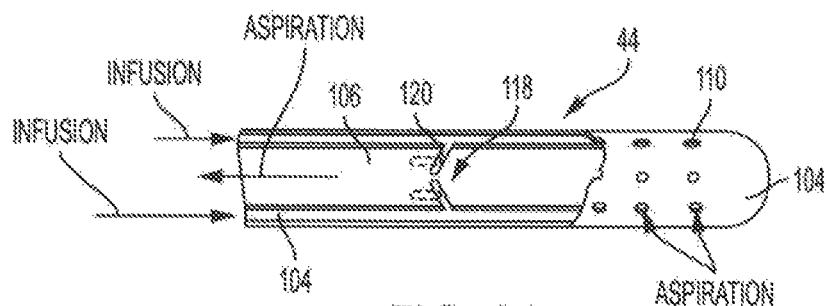
FIG. 21 is a partial cross-sectional view of a distal tip of a catheter including a valve according to an aspect of the present disclosure taken along line B-B.

As shown in FIG. 21, in one aspect of the valve 118, one or more inflatable valve leaflets 120 are provided in the lumen of the multi-lumen catheter 44. The leaflets 120 function so that flow in an aspiration lumen 106 may be reduced or occluded by the introduction of fluid pressure in an infusion lumen 104 or a plurality of infusion lumina, causing the expansion, deployment or deflection of said leaflets 120. The valve leaflets 120 move from a first, open position to a second, closed position upon filling in response to infusion fluid pressure. The leaflets 120 may be elastic or non-elastic, porous or non-porous. The leaflets 120 may return to an open position, opposed to the first lumen wall, by passive reaction to reduction in pressure, flow of aspirated fluids, and/or folding memory in the leaflet membrane. A valve, such as a check valve, may be provided in the infusion lumen 104, proximally to the leaflets 120, to cause infusion fluid to exit through the leaflet membrane.

Figure 22:
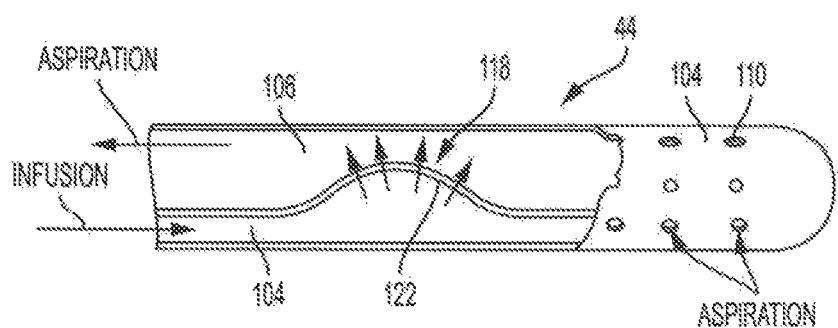
FIG. 22 is a partial cross-sectional view of a distal tip of a catheter including a valve according to another aspect of the present disclosure taken along line B-B.

With reference to FIG. 22, one aspect of the valve 118 enables a valve function by inclusion of at least one expandable balloon 122 in the lumina of the catheter 44 so that flow in an aspiration lumen 106 may be reduced or occluded by the introduction of pressure in an infusion lumen 104, causing the expansion of the balloon(s) 122. The balloon 122 may be included in the wall of the infusion lumen 104 as an elastic or non-elastic membrane between lumina. The balloon 122 may also be porous or non-porous so that infusion fluid may enter the aspiration lumen 106 through the porous membrane, separately through apertures 110, or via a separate lumen. A valve, such as a check valve, may be provided in the infusion lumen 104, proximally to the balloon 122, to cause infusion fluid to exit through the balloon membrane. The balloon 122 may expand by increased pressure in the infusion lumen 104 and collapse by reduction in pressure resulting from balloon membrane leakage, infusion into the aspiration lumen 106, or change in pressure caused by a controller.

With restriction of aspiration flow by a balloon valve 122, infusion flow may be better directed to the aspiration lumen 106 without uncontrolled losses of infused fluids to the aspiration lumen 106. This dynamic can be implemented to keep apertures 110 clear of debris, agitate media surrounding the catheter 44, or provide a desired flow or pressure to the body cavity or tissue.

Figure 23:
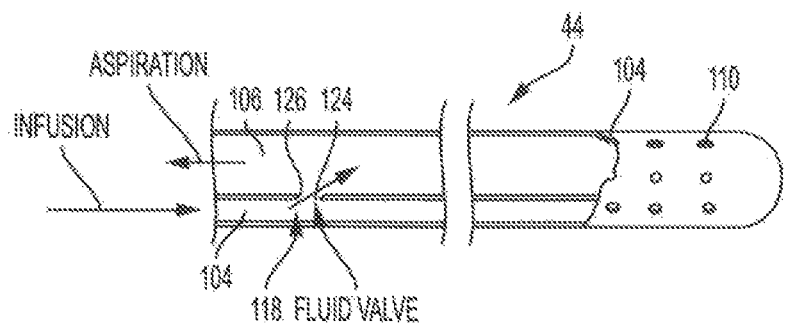
FIG. 23 is a partial cross-sectional view of a distal tip of a catheter including a valve according to another aspect of the present disclosure taken along line B-B.

With reference to FIG. 23, in one aspect of the catheter 44, flow in an aspiration lumen 106 of a multi-lumen catheter 44 is reduced or stopped by the introduction of flow and fluid pressure 124 in an opposite direction from an infusion lumen 104 into the same aspiration lumen 106. Aspiration flow through the aspiration lumen 106 takes place under relatively high frictional flow resistance as a result of small lumen cross-sectional dimensions over long catheter lengths (for example, lengths greater than 5 cm). Flow resistance is a function of fluid viscosity, flow area, and length. Therefore, if a fluid valve or port 126 allowing infusion flow 124 from the infusion lumen 104 into the aspiration lumen 106 is placed at a relatively long length (for example, lengths greater than 5 cm) proximally from the apertures 110 at the distal tip of the catheter 44, infusion flow 124 and pressure provided by the infusion lumen 104 at the fluid valve or port 126, in a direction substantially opposed to aspiration flow, would restrict flow in the aspiration lumen 106. In this manner, a valve 118 could be provided within the catheter 44 or tube set 36 so that a valve function is provided without any mechanical displacement of flow obstacles within the catheter 44 and without the requirement of the construction or manufacture of mechanical valve structures within the catheter 44.

A variety of additional features or functions may also be included in the fluid exchange 2 system of the present disclosure. For example, features may be included in the catheter 44 of the fluid exchange system 2 to facilitate use of the catheter 44 by a clinician or doctor, improve the feel of the catheter 44 while in use, and provide both safety for the patient and confidence in low risk use for the clinician. These catheter features include an atraumatic distal tip designed to be compatible with the intended surrounding body tissues and steerability of the catheter 44, including the use of one or several guidewires, one or several sheaths and/or other surgical navigation means and methods, for safer and more effective introduction into the body cavity or target tissue.

In addition to measuring and managing flow, the system 2 of the present disclosure may also include sensors, algorithms and related methods of use and specific placement thereof to characterize either or both of the infused and aspirated fluids. Fluid characteristics may include aeration, bubble content, solid or particulate content, fluid density, fluid-borne particle dispersion, color, hemoglobin, biological content, molecular and nanoparticle content (including pharmaceutical agents), and additional physical fluid properties such as density, pH, radioactivity and electrical properties. For example, the control unit 4 may include an ultrasound sensor generally positioned as a cuff or horseshoe around the tube set 36 to detect bubbles and particulate in the aspirated (or even infused) fluids. Pressure sensors, located along any segment or component of fluid flow, may also be used to detect pressure drops or differentials to indicate changes in fluid properties, air inclusions, or flow restriction. Sensors may also be included in or positioned on the fluid source 10 and/or drainage receptacle 12 to indicate fluid level in the container and characterize the contained fluid as listed above. Load sensors and fluid level sensors may also be included to indicate the weight and volume of aspirated fluid as well as the rate of aspiration of fluids as well as infusion of fluids. Also, optical flow sensors measuring drops in the drip chambers of infusion and aspiration containers can be used to monitor infused and aspirated fluid volumes.

The system 2 may also include an output device for providing a signal output in correspondence to the determined cerebral compliance. The liquid infusion into said intracranial cavity can include an opium alkaloid antispasmodic drug, preferably papaverine, or any other drug appropriate to the intended therapy.

The system 2 may be used for a variety of reasons identified by a medical personnel. The medical personnel may wish to drain a hematoma of a patient in a safe way without catheter clogging, since normal hematoma drainage systems suffer from clogged catheters. The medical personnel may wish to monitor ICP of the patient since ICP is a good indication of current patient state. The medical personnel may wish to be able to set low and high pressure alarm levels, since changes in patient state should be identified to the medical personnel. The medical personnel may wish to extract a log file containing treatment details from the control unit 4 to attach to a patient's medical record, since knowing what happened when is important in critical care. The medical personnel may wish to use a device that operates using battery power, since there may be a need to move the patient while the system 2 is performing treatment. The medical personnel may wish to change the fluid flow rate, since different fluid flow rates are needed depending on the patient's state. The medical personnel may wish to see the current pressure in the patient's brain, since the pressure varies up and down faster than the ICP measurement. The medical personnel may wish to stop the treatment and restart the treatment at a later point, since the system may need to be disconnected from a patient during, for example, a CT scan. The medical personnel may wish to avoid infusing air into the patient when the fluid source is empty, since infusion of large amounts of air could be harmful to the patient. The medical personnel may wish to view the battery charge level, since this determines how long the device can run on the current battery. The medical personnel may wish to make sure the time and date is accurate before treatment starts, since the log extracted and attached to the patient medical record must have accurate dates and times. The medical personnel may wish to see the current treatment phase, since this explains the pressure variations of the current pressure of the patient's brain. The medical personnel may also wish to see the elapsed treatment time.

According to a further aspect, the present disclosure relates to a method of treating a patient including the step of administering to a patient in need of at least one drug by a catheter 44 or system 2 of the present disclosure. An even further aspect herein is a drug or drug combination for use in a method for treatment of the human or animal body by surgery or therapy, wherein a catheter 44 or system 2 of the present disclosure is used in said method. Preferably, in the latter aspects, the drug or drug combination is administered to a patient by a catheter 44 or system 2 of the present disclosure. Preferably, a drug combination includes at least two drugs. A related aspect herein is a drug or drug combination for use in a diagnostic method practiced on the human or animal body, in which a catheter 44 or system 2 of the present disclosure is used in said method. In a particular aspect, a diagnostic agent is administered to a patient by a catheter 44 or system 2 of the present disclosure.

Many advantages of the present disclosure will be apparent to those skilled in the art with a reading of this disclosure. It will be appreciated that the various components and aspects described herein are merely illustrative embodiments and that the present disclosure (or components or aspects thereof) may extend beyond the specific clinical indication of cerebral vasospasm. For example, the fluid exchange system 2 as well as the respective methods as disclosed herein may have broad applicability to other areas of medicine, including but not limited to therapy involving the delivery of drugs or therapeutic agents and their antidotes for thrombolysis, coagulation, chemotherapy, infection management, hormone therapy, cell seeding, cell therapy, markers, and therapies applied directly to the targeted surrounding tissue. The fluid exchange system 2 of the present disclosure can both serve all surgical drainage needs as well as all invasive local drug delivery needs.

While various aspects of the system and the user interface and methods of operating the user interface were provided in the foregoing description, those skilled in the art may make modifications and alterations to these aspects without departing from the scope and spirit of the disclosure. For example, it is to be understood that this disclosure contemplates that, to the extent possible, one or more features of any aspect may be combined with one or more features of any other aspect. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A fluid exchange system, comprising:
   a control unit comprising a processor;
   a tube set attachment removably connected to the control unit, the tube set attachment comprising a tube set fluidly connected to a fluid source and a drainage receptacle;
   a catheter fluidly connected to the tube set; and
   at least one sensor connected to at least one of the control unit and the tube set attachment,
   wherein the control unit is configured to supply fluid to a patient through the tube set and drain fluid from the patient via the tube set, and
   wherein the control unit is configured to receive intracranial pressure measurements from the at least one sensor to adjust the supply of the fluid to the patient and the drainage of the fluid from the patient,
   wherein the control unit is further configured to receive a first intracranial pressure measurement from the at least one sensor, initiate infusion of the fluid into the patient, and receive a second intracranial pressure measurement from the at least one sensor after the infusion of the fluid,
   wherein, in an event a difference between the first intracranial pressure measurement and the second intracranial pressure measurement exceeds a first pressure threshold value or is less than a second pressure threshold value, the control unit is configured to issue a pressure signal output to indicate the first pressure threshold value has been exceeded or the difference between the first and the second intracranial pressure measurements is less than the second pressure threshold value, wherein the control unit is further configured to initiate the drainage of the fluid from the patient in the event the difference between the first and the second intracranial pressure measurements from the at least one sensor exceeds the first pressure threshold value, and wherein the control unit is further configured to initiate additional infusion of the fluid into the patient in the event the difference between the first and the second intracranial pressure measurements from the at least one sensor falls below the second threshold value.

2. The fluid exchange system as recited in claim 1, wherein the at least one sensor comprises a pressure sensor.

3. The fluid exchange system as recited in claim 2, wherein the at least one sensor is positioned in a cassette of the tube set attachment.

4. The fluid exchange system as recited in claim 1, wherein the at least one sensor comprises a pressure sensor,
wherein the at least one sensor is positioned in the control unit.

5. The fluid exchange system as recited in claim 1, wherein the fluid supplied by the control unit comprises a pharmaceutical drug or therapeutic agent.

6. The fluid exchange system as recited in claim 1, wherein the catheter comprises:
a first lumen comprising a proximal end and a distal end;
a second lumen disposed within the first lumen and comprising a proximal end and a distal end;
a valve disposed within at least one of the first lumen and the second lumen and configured to control a flow of fluid through the catheter; and
a sleeve provided on the distal ends of the first and second lumens.

7. The fluid exchange system as recited in claim 6, wherein at least one aperture is defined in at least one of the first lumen and the second lumen,
wherein the sleeve is axially displaceable relative to the first lumen and the second lumen, and
wherein the sleeve is moveable between a first position in which the at least one aperture is covered by the sleeve and a second position in which the at least one aperture is not covered by the sleeve.

8. The fluid exchange system as recited in claim 6, wherein at least one aperture is defined in at least one of the first lumen and the second lumen,
wherein the sleeve is rotationally displaceable relative to the first lumen and the second lumen, and
wherein the sleeve is moveable between a first position in which the at least one aperture is covered by the sleeve and a second position in which the at least one aperture is not covered by the sleeve.

9. The fluid exchange system as recited in claim 1, wherein the tube set attachment further comprises a cassette configured to removably connect the tube set attachment to the control unit.

10. The fluid exchange system as recited in claim 1, wherein the control unit further comprises a pump to supply fluid from the fluid source to the patient via the tube set.

11. The fluid exchange system as recited in claim 1, wherein the tube set comprises a first tube fluidly connected to the fluid source at a first end and the catheter at a second end, and a second tube fluidly connected to the catheter at a first end and the drainage receptacle at a second end.

12. The fluid exchange system as recited in claim 1, wherein the fluid source comprises an infusion bag.

13. The fluid exchange system as recited in claim 1, wherein the drainage receptacle comprises an aspiration bag.

14. The fluid exchange system as recited in claim 1, wherein the drainage receptacle is connected to the control unit via a graduated measuring band, the graduating measuring band being configured to permit the drainage receptacle to be arranged vertically upright to the control unit.

15. The fluid exchange system as recited in claim 1, wherein the drainage receptacle is adjustable in a vertical direction relative to the control unit.

16. The fluid exchange system as recited in claim 1, wherein the tube set attachment further comprises at least one pressure sensor to measure a pressure of the fluid flowing through the tube set.

17. The fluid exchange system as recited in claim 1, wherein the tube set attachment is disposable.

18. The fluid exchange system as recited in claim 1, wherein the tube set attachment includes a security valve positioned between a portion of the tube set and a cassette fluidly connected to the tube set.

19. The fluid exchange system as recited in claim 1, wherein the control unit further comprises a graphical user interface comprising at least a flow rate indicator and an intracranial pressure alarm that monitors intracranial pressure levels in a patient connected to the fluid exchange system.

20. The fluid exchange system as recited in claim 19, wherein the intracranial pressure alarm includes a high intracranial pressure threshold alarm and a low intracranial pressure threshold alarm.

21. The fluid exchange system as recited in claim 1, wherein the control unit further comprises an air sensor connected to a portion of the tube set to identify when the fluid source is empty.

22. The fluid exchange system of claim 1, wherein the control unit is further configured to:
supply or drain fluid to a patient according to a preprogrammed treatment process,
stop the preprogrammed treatment process in the event the difference between the first and the second intracranial pressure measurements exceeds the first pressure threshold value or is less than the second pressure threshold value, and
resume the preprogrammed treatment process when the difference between the first and the second intracranial pressure measurements is less than the first pressure threshold value and exceeds the second pressure threshold value.

* * * * *

UNITED STATES PATENT AND TRADEMARK OFFICE
CERTIFICATE OF CORRECTION

| | |
|---|---|
| PATENT NO. | : 12,042,597 B2 |
| APPLICATION NO. | : 16/489774 |
| DATED | : July 23, 2024 |
| INVENTOR(S) | : Christos Panotopoulos et al. |

It is certified that error appears in the above-identified patent and that said Letters Patent is hereby corrected as shown below:

In the Specification

Column 1, Line 10, delete "62/473,301, filed Mar. 17, 2017" and insert -- 62/473,303 filed Mar. 17, 2017, --

Column 1, Line 13, delete "62/470,711," and insert -- 62/470,711 --

Signed and Sealed this
First Day of October, 2024

Katherine Kelly Vidal
*Director of the United States Patent and Trademark Office*